(12) United States Patent
Bryan et al.

(10) Patent No.: US 7,025,787 B2
(45) Date of Patent: Apr. 11, 2006

(54) IMPLANTABLE JOINT PROSTHESIS AND ASSOCIATED INSTRUMENTATION

(75) Inventors: Vincent Bryan, Mercer Island, WA (US); Alex Kunzler, Issaquah, WA (US); Randall Allard, North Bend, WA (US); Richard Broman, Kirkland, WA (US); Anthony Finazzo, Lake Forest Park, WA (US); Carlos Gil, Sammamish, WA (US); Elliott Marshall, Seattle, WA (US); Leonard Tokish, Issaquah, WA (US)

(73) Assignee: SDGI Holdings, Inc., Wilmington, DE (US)

( * ) Notice: Subject to any disclaimer, the term of this patent is extended or adjusted under 35 U.S.C. 154(b) by 69 days.

(21) Appl. No.: 10/303,569

(22) Filed: Nov. 25, 2002

(65) Prior Publication Data
US 2003/0135277 A1 Jul. 17, 2003

Related U.S. Application Data

(60) Provisional application No. 60/333,627, filed on Nov. 26, 2001.

(51) Int. Cl.
*A61F 2/44* (2006.01)
(52) U.S. Cl. .................... 623/17.16; 623/17.15
(58) Field of Classification Search ... 623/17.11–17.16
See application file for complete search history.

(56) References Cited

U.S. PATENT DOCUMENTS

| | | | |
|---|---|---|---|
| 3,486,505 A | 12/1969 | Morrison | |
| 3,574,374 A | 4/1971 | Keller et al. | |
| 3,875,595 A | 4/1975 | Froning | |
| 3,876,728 A | 4/1975 | Stubstad | |
| 4,023,572 A | 5/1977 | Weigand et al. | |
| 4,116,200 A | 9/1978 | Braun et al. | |
| 4,179,810 A | 12/1979 | Kirsch | |
| 4,309,777 A | 1/1982 | Patil | |
| 4,349,921 A | 9/1982 | Kuntz | |
| 4,645,507 A | 2/1987 | Engelbrecht et al. | |
| 4,706,659 A | 11/1987 | Matthews et al. | |
| 4,714,469 A | 12/1987 | Kenna | |
| 4,743,256 A | 5/1988 | Brantigan | |
| 4,757,983 A | 7/1988 | Ray et al. | |
| 4,759,766 A | 7/1988 | Buettner-Janz et al. | |
| 4,759,769 A | 7/1988 | Hedman et al. | |
| 4,766,328 A | 8/1988 | Yang | |

(Continued)

FOREIGN PATENT DOCUMENTS

DE 2263842 7/1974

(Continued)

OTHER PUBLICATIONS

Brain, et al., "The Neurological Manifestations of Cervical Spondylosis", Brain: A Journal of Neurology, vol. 75; Macmillan & Co.; 1952; pp. 187-225.

(Continued)

*Primary Examiner*—David O. Reip
(74) *Attorney, Agent, or Firm*—Haynes and Boone, LLP

(57) ABSTRACT

An implantable prosthesis is described having a pair of opposed shells and a central body disposed between the opposed shells wherein the central body and the shells cooperate to limit the motion of the central body with respect to the shells. An assembly for preparing a disc space for the implantation of a prosthesis is further described having a plurality of instruments cooperating to guide a tool associated with the assembly.

22 Claims, 19 Drawing Sheets

U.S. PATENT DOCUMENTS

| | | |
|---|---|---|
| 4,777,942 A | 10/1988 | Frey et al. |
| 4,800,639 A | 1/1989 | Frey et al. |
| 4,834,757 A | 5/1989 | Brantigan |
| 4,863,476 A | 9/1989 | Shepperd |
| 4,863,477 A | 9/1989 | Monson |
| 4,874,389 A | 10/1989 | Downey |
| 4,878,915 A | 11/1989 | Brantigan |
| 4,887,595 A | 12/1989 | Heinig et al. |
| 4,904,260 A | 2/1990 | Ray et al. |
| 4,904,261 A | 2/1990 | Dove et al. |
| 4,908,032 A | 3/1990 | Keller |
| 4,908,036 A | 3/1990 | Link et al. |
| 4,911,718 A | 3/1990 | Lee et al. |
| 4,917,704 A | 4/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 4,978,355 A | 12/1990 | Frey et al. |
| 4,997,432 A | 3/1991 | Keller |
| 5,002,576 A | 3/1991 | Fuhrmann et al. |
| 5,015,247 A | 5/1991 | Michelson |
| 5,035,716 A | 7/1991 | Downey |
| 5,047,055 A | 9/1991 | Bao et al. |
| 5,059,193 A | 10/1991 | Kuslich |
| 5,059,194 A | 10/1991 | Michelson |
| 5,062,845 A | 11/1991 | Kuslich et al. |
| 5,071,437 A | 12/1991 | Steffee |
| 5,080,662 A | 1/1992 | Paul |
| 5,084,048 A | 1/1992 | Jacob et al. |
| 5,108,438 A | 4/1992 | Stone |
| 5,122,130 A | 6/1992 | Keller |
| 5,123,926 A | 6/1992 | Pisharodi |
| 5,171,280 A | 12/1992 | Baumgartner |
| 5,171,281 A | 12/1992 | Parsons et al. |
| 5,176,708 A | 1/1993 | Frey et al. |
| 5,192,327 A | 3/1993 | Brantigan |
| 5,236,460 A | 8/1993 | Barber |
| 5,258,031 A | 11/1993 | Salib et al. |
| 5,261,913 A | 11/1993 | Marnay |
| 5,306,308 A | 4/1994 | Gross et al. |
| 5,314,477 A | 5/1994 | Marnay |
| 5,314,478 A | 5/1994 | Oka et al. |
| 5,320,644 A | 6/1994 | Baumgartner |
| 5,383,933 A | 1/1995 | Keller |
| 5,401,269 A | 3/1995 | Buttner-Janz et al. |
| 5,403,314 A | 4/1995 | Currier |
| 5,425,772 A | 6/1995 | Brantigan |
| 5,425,773 A | 6/1995 | Boyd et al. |
| 5,443,514 A | 8/1995 | Steffee |
| 5,456,719 A | 10/1995 | Keller |
| 5,458,638 A | 10/1995 | Kuslich et al. |
| 5,458,642 A | 10/1995 | Beer et al. |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland et al. |
| 5,507,816 A | 4/1996 | Bullivant |
| 5,514,180 A | 5/1996 | Heggeness et al. |
| 5,527,315 A | 6/1996 | Jeanson et al. |
| 5,534,028 A | 7/1996 | Bao et al. |
| 5,545,229 A | 8/1996 | Parsons et al. |
| 5,556,431 A | 9/1996 | Buttner-Janz |
| 5,562,738 A | 10/1996 | Boyd et al. |
| 5,571,109 A | 11/1996 | Bertagnoli |
| 5,593,409 A | 1/1997 | Michelson |
| 5,609,636 A | 3/1997 | Kohrs et al. |
| 5,645,598 A | 7/1997 | Brosnahan |
| 5,649,926 A | 7/1997 | Howland |
| 5,658,285 A | 8/1997 | Marnay et al. |
| 5,662,158 A | 9/1997 | Caldarise |
| 5,674,294 A | 10/1997 | Bainville et al. |
| 5,674,295 A | 10/1997 | Ray et al. |
| 5,674,296 A | 10/1997 | Bryan et al. |
| 5,683,464 A | 11/1997 | Wagner et al. |
| 5,702,450 A | 12/1997 | Bisserie |
| 5,713,899 A | 2/1998 | Marnay et al. |
| 5,716,415 A | 2/1998 | Steffee |
| 5,720,748 A | 2/1998 | Kuslich et al. |
| 5,722,977 A | 3/1998 | Wilhelmy |
| 5,723,013 A | 3/1998 | Jeanson et al. |
| 5,741,253 A | 4/1998 | Michelson |
| 5,782,830 A | 7/1998 | Farris |
| 5,782,832 A | 7/1998 | Larsen et al. |
| 5,797,909 A | 8/1998 | Michelson |
| 5,824,093 A | 10/1998 | Ray et al. |
| 5,824,094 A | 10/1998 | Serhan et al. |
| 5,865,846 A | 2/1999 | Bryan et al. |
| 5,865,848 A | 2/1999 | Baker |
| 5,885,300 A | 3/1999 | Tokuhashi et al. |
| 5,888,197 A | 3/1999 | Mulac et al. |
| 5,888,226 A | 3/1999 | Rogozinski |
| 5,897,087 A | 4/1999 | Farley |
| 5,902,233 A | 5/1999 | Farley et al. |
| 5,928,284 A | 7/1999 | Mehdizadeh |
| 5,947,971 A | 9/1999 | Kuslich et al. |
| 5,976,187 A | 11/1999 | Richelsoph |
| 5,984,865 A | 11/1999 | Farley et al. |
| 5,989,291 A | 11/1999 | Ralph et al. |
| 6,001,130 A | 12/1999 | Bryan et al. |
| 6,017,008 A | 1/2000 | Farley |
| 6,022,376 A | 2/2000 | Assell |
| 6,033,363 A | 3/2000 | Farley et al. |
| 6,059,790 A | 5/2000 | Sand et al. |
| 6,059,829 A | 5/2000 | Schlapfer et al. |
| 6,063,121 A | 5/2000 | Xavier et al. |
| 6,066,174 A | 5/2000 | Farris |
| 6,080,155 A | 6/2000 | Michelson |
| 6,083,228 A | 7/2000 | Michelson |
| 6,086,595 A | 7/2000 | Yonemura et al. |
| 6,096,038 A | 8/2000 | Michelson |
| 6,139,579 A | 10/2000 | Steffee et al. |
| 6,156,067 A | 12/2000 | Bryan et al. |
| 6,162,252 A | 12/2000 | Kuras et al. |
| 6,228,022 B1 | 5/2001 | Friesem et al. |
| 6,228,026 B1 | 5/2001 | Rull et al. |
| 6,231,609 B1 | 5/2001 | Mehdizadeh |
| 6,478,800 B1 | 11/2002 | Fraser et al. |
| 6,673,113 B1 * | 1/2004 | Ralph et al. ............ 623/17.13 |
| 2002/0128715 A1 | 9/2002 | Bryan et al. |
| 2002/0151901 A1 | 10/2002 | Bryan et al. |

FOREIGN PATENT DOCUMENTS

| | | |
|---|---|---|
| DE | 2804936 | 8/1979 |
| DE | 30 23 353 A1 | 4/1981 |
| DE | 37 41 493 A1 | 6/1989 |
| DE | 196 53 580 | 6/1998 |
| EP | 0176728 | 4/1986 |
| EP | 0 560 140 A1 | 9/1993 |
| GB | G 90 00 094.3 | 3/1991 |
| SU | 895433 | 1/1982 |
| SU | 1560184 | 4/1990 |
| WO | WO 00/04839 | 2/2000 |
| WO | WO 00/04851 | 2/2000 |
| WO | WO 00/13619 | 3/2000 |
| WO | WO 00/13620 | 3/2000 |
| WO | WO 02 11633 | 2/2002 |

OTHER PUBLICATIONS

Buttner-Janz, et al.; "Biomechanics of the SB Charite Lumbar Intervertebral Disc Endoprosthesis"; International Orthopedics; vol. 13; 1989; pp. 173-176.

Edeland; "Some Additional Suggestions for an Intervertebral Disc Prosthesis"; Dept. of Occupational Health; Vdvo PV AB; S-40508; Goteborg; Sweden; 1985 Butterworth & Co. Publishers Ltd.

Enker et al.; "Artificial Disc Replacement"; Spine; vol. 18; No. 8; 1993; pp. 1061-1070.

Hawkins, et al.; "Shear Stability of an Elastomeric Disk Spacer Within an Intervertebral Joint: A Parametric Study"; Journal of Biomechanical Engineering Technical Briefs; vol. 114; Aug. 1992; pp. 414-415.

Hedman, et al.; "Design of an Intervertebral Disc Prosthesis"; Spine; vol. 17; No. 6; 1991; pp. S256-S260.

Hellier, et al.; "Wear Studies for Development of an Intervertebral Disc Prosthesis"; Spine; vol. 17; No. 6 Supplement; 1992; S86-S96.

Hood; "Far Lateral Lumbar Disc Herniations"; Neurosurgery Clinics of North America; vol. 4, No. 1; Jan. 1993; pp. 117-124.

Langrana, et al.; "Finite-Element Modeling of the Synthetic Intervertebral Disc"; Spine; vol. 16; No. 6: 1991; pp. S245-S252.

Lee, et al.; "Development of a Prosthetic Intervertebral Disc"; Spine; vol. 16; No. 6; 1991; pp. S253-S255.

Lees, et al.; "Natural History & Prognosis of Cervical Spondylosis"; British Medical Journal; Dec. 28, 1963; British Medical Association, London, England; Copyright 1963; pp. 1607-1610.

Long; "Failed Back Surgery Syndrome"; Neurosurgery Clinics of North America; vol. 2, No. 4; Oct. 1991; pp. 899-919.

Ray; "The Artificial Disc-Introduction, History and Socioeconomics"; Clinical Efficacy and Outcome in the Diagnosis and Treatment of Low Back Pain; Raven Press, Ltd., NY; 1992; pp. 205-280.

Robinson, et al.; "The Results of Anterior Interbody Fusion of the Cervical Spine"; The Journal of Bone & Joint Surgery; vol. 44-A, No. 8, Dec. 1962; pp. 1569-1587.

Simeone and Rothman; "Cervical Disc Disease"; Pennsylvania Hospital & University of Pennsylvania; 1975; pp. 387-433.

Solini, et al.; "Metal Cementless Prosthesis for Vertebral Body Replacement of Metastatic Malignant Disease of the Cervical Spine"; Journal of Spinal Disorders; vol. 2; No. 4; 1989; pp. 254-262.

Taylor, Collier; "The Occurence of Optic Neuritis in Lesions of the Spinal Cord, Injury, Tumor, Melitis"; Brain: A Journal of Neurology; vol. 24; Macmillian & Co. Ltd, 1901; pp. 532-550.

Tie-sheng, et al.; "Lumbar Intervertebral Disc Prosthesis"; Chinese Medical Journal. 104-(5); 1991; pp. 381-386.

\* cited by examiner

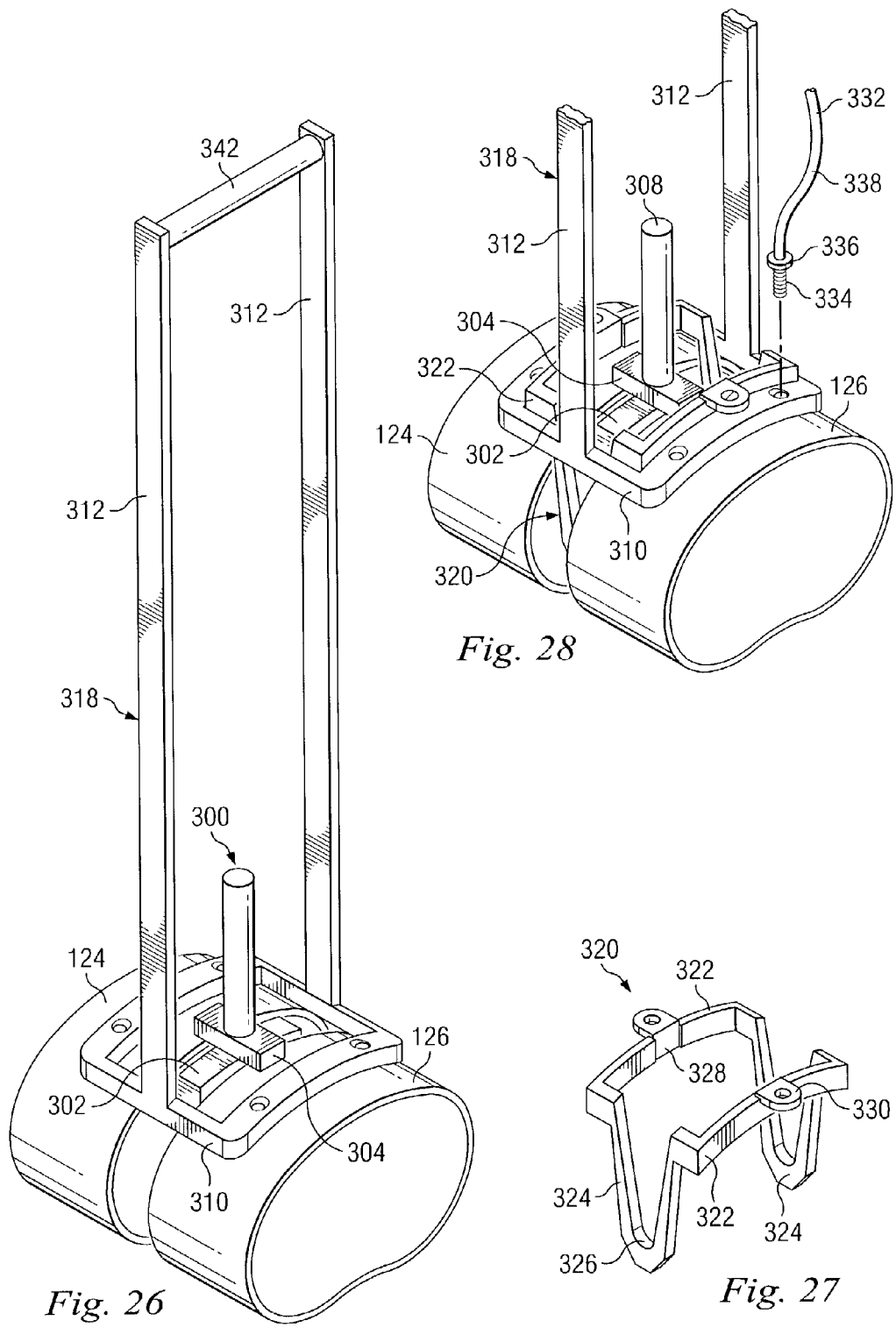

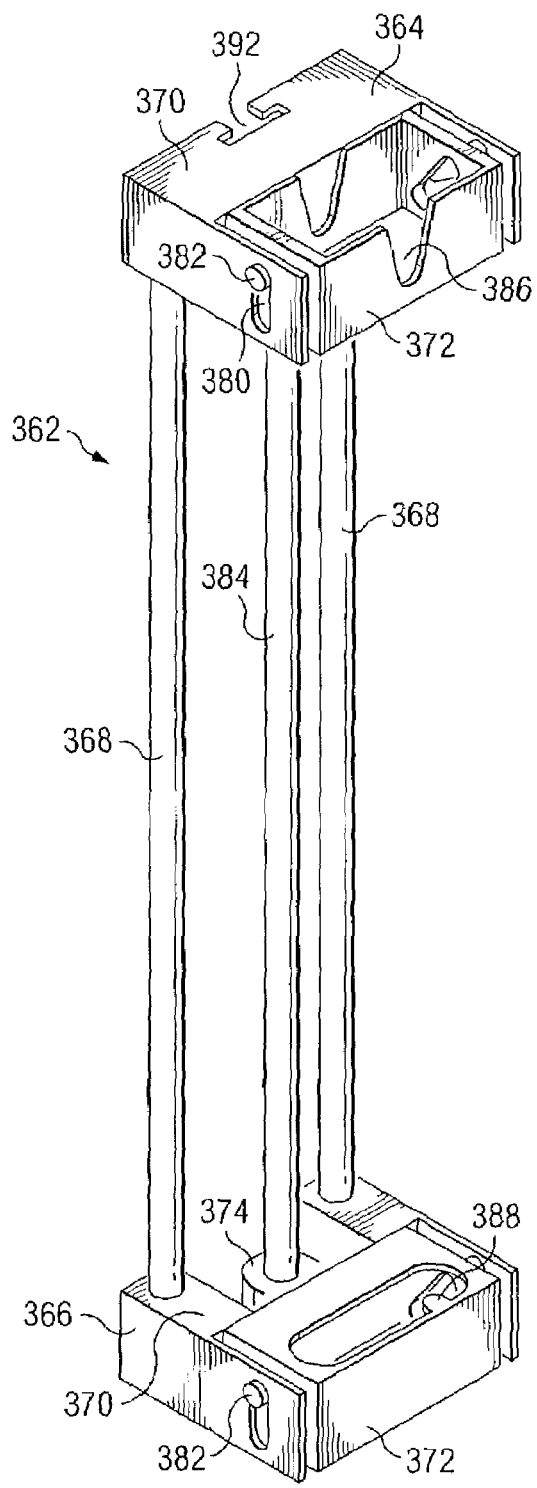
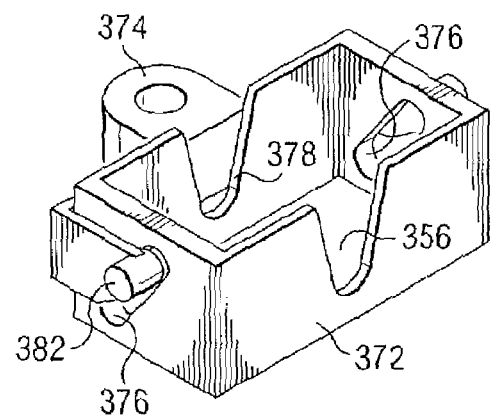
FIG. 32B
FIG. 32A

IMPLANTABLE JOINT PROSTHESIS AND ASSOCIATED INSTRUMENTATION

CROSS-REFERENCE TO RELATED APPLICATION

This application claims priority to the provisional application filed on Nov. 26, 2001 (U.S. Ser. No. 60/333,627). This provisional application is herein incorporated by reference for all legitimate purposes.

BACKGROUND

According to one embodiment, implantable prostheses are provided that are suitable for replacement of diarthroidal or arthroidal joints by creating an artificial diarthroidal-like joint at the site of the implant.

In a particular embodiment, an implantable prosthesis is described serving as a replacement for at least a portion of the intervertebral disc material, i.e., a spinal disc endoprostheses suitable for implantation in vertebrates, including humans.

In another embodiment, an assembly with associated instrumentation is described for preparing a disc space for the insertion of a prosthesis.

Many joints in the human body, such as hips, knees, shoulders, etc., are diarthroidal, meaning that the joints include a joint capsule that is filled with fluid. The capsule fluid lubricates the joint, and allows the surfaces of the joint to move with a low coefficient of friction. The spine, by contrast, can be considered to be a series of joints, some of which (the anterior joint or disc) lack a fluid filled capsule and are therefore arthroidal (the spine also contains facet joints that are diarthroidal). The interior portion of intervertebral discs are not provided by the body with significant blood supply; their homeostasis is enhanced by the diffusion of fluids into the disc tissue, thus supplying them with nutrients. This, to some extent, allows the tissue to grow and repair damage done by stress as the joint moves. Despite this process, in mature adults, spinal disc tissue degrades continuously over time. Sufficiently advanced degeneration can lead to herniation or rupture of the spinal disc.

Herniation of a spinal disc can result in a number of debilitating symptoms, including intractable pain, weakness, and sensory loss. Treatment of these symptoms frequently requires surgical removal of at least a portion of the herniated disc, a procedure known as discectomy. Often discectomy alone cannot stop the progressive degeneration at the level of disc excision. An additional procedure is often performed in conjunction with the discectomy with the objective of fusing together (arthrodesis) the vertebral bodies surrounding the affected disc space. This is accomplished by removing the cartilaginous endplates by scraping the surfaces of the vertebral body and inserting a piece of graft bone, which may be an allograft from a bone bank, or an autograft, typically taken from the iliac crest of the patient, or other suitable material.

The discectomy and arthrodesis procedures can be problematic, however. Discectomy problems have been described above. The grafting or fusion procedure has a variable success rate of about 80%, and even when successful, requires considerable recovery time before fusion is complete. Perhaps of even greater concern, successful fusion eliminates normal spinal biomechanics. Range of motion at the level of the fusion is ideally eliminated, because the affected vertebrae have been effectively joined to form a single bone. Because the patient tries to maintain the same overall range of motion of the entire spine, additional stress is imposed on the intervertebral discs of the adjacent vertebrae. This, in turn, may lead to accelerated degeneration at levels above and below the fusion site, which may require additional treatment, including discectomy and fusion. Grafting procedures carry some risk of tissue rejection and disease transmission if an allograft is used, and risk of harvest site morbidity when the patient's own tissue is harvested.

As a result of these difficulties with intervertebral fusion, attempts have been made to provide a prosthetic solution to degenerative disc disease that maintains the patient's normal spinal biomechanics, allows for shorter recovery times, and avoids the complications inherent in harvesting and/or grafting bone tissue. Some of these efforts have centered around providing an endoprosthetic intervertebral implant, as described in U.S. Pat. Nos. 5,865,846, 5,674,296, 5,989,291, 6,001,130, 6,022,376, and pending U.S. patent application Ser. No. 09/924,298, filed on Aug. 8, 2001, the entire contents of which are hereby incorporated by reference.

Design and construction of such an implant, however, is not simple. Desirably, the implant should be precisely placed in a prepared intervertebral space, and should contain elements that are immobilized with respect to each of the vertebral bodies, so that the implant does not migrate or shift, potentially contacting, abrading, or otherwise damaging the spinal cord, ligaments, blood vessels, and other soft tissue. At the same time, the implant should allow the vertebral bodies to move relative to each other in a way that provides the equivalent motion afforded by a healthy intervertebral disc, and that allows the affected vertebral joint to participate in the coordinated overall movement of the spine in a way that closely approximates the natural movement of a healthy spinal column. The implant should be biocompatible, and avoid the introduction of toxic or harmful components into the patient, such as release of wear debris. The implant should also restore normal disc height and maintain the patient's vertebral lordosis, and should not allow any significant post-operative subsidence. The implant should be at least partially constrained by soft tissue in and around the intervertebral space, in order to allow a simpler, more efficient design. There remains a need for a device which would decrease patient recovery time, and reduce the occurrence of postoperative degeneration at levels above and below the implant, as compared with fusion techniques. In addition, such an implant would avoid the need for harvesting of autograft bone tissue, thereby eliminating morbidity at the harvesting site. Such an implant should also provide elasticity and damping sufficient to absorb shocks and stresses imposed on it in a manner similar to that of the natural spinal disc.

Furthermore, specially designed instrumentation should be provided to facilitate the precise placement of the implant. The instrumentation should facilitate accurate preparation of the vertebral body endplates to receive the implant, but should be minimally obtrusive of the surgeon's view of the operating site. The instrumentation should be adapted for use in an anterior surgical approach to the lumbar spine where there are numerous structures that are at risk, and which if damaged could cause severe complications.

SUMMARY

This invention satisfies the needs and concerns described above. Other concerns can arise that are more unique to any joint replacement or reconstruction, particularly with respect to device stability, range of motion, and postoperative material degradation. In general, in patients undergoing joint replacement, the patient's condition and quality of life is improved more by a technique that provides a range of motion that more closely approximates the range of motion of a healthy joint (assuming that this can be done in a safe manner) than by a technique that provides a decreased range of motion. Important parts of accomplishing this goal include using an implant design that is highly stable when implanted, and making use of the soft tissue associated with the joint (to the extent possible) to stabilize the implant and leave restriction of some of the motion of the joint to the soft tissue. This allows the implant design to be considerably simpler. Irrespective of the joint being implanted, an implant that provides an effectively sealed, fluid filled capsule (i.e., an artificial diarthroidal-like joint) will likely provide an added margin of safety because the moving surfaces are isolated from the surrounding tissue and body fluids, and the environment in which the moving surfaces operate can be engineered and controlled. The lubrication effects in such a joint allow it to function more effectively and potentially generate less wear debris. Any wear debris that is generated, however, is contained within the implant and will not come into contact with live tissue or body fluids. Similarly, tissue ingrowth into the articulating regions of the implant and degradation of the implant materials by body fluids are also avoided.

In one embodiment, a surgical implant is provided where the structure of the implant contains cooperating features that allows a joint into which the implant has been inserted to closely approximate the biomechanics and motion of a healthy joint.

In this embodiment, the implant contains two rigid opposing plates or shells, each having an outer surface adapted to engage the prepared surfaces of the bones of a joint in such a way that frictional forces resist movement of the plates or shells relative to the bone surface. The outer surfaces are sufficiently rough that frictional forces strongly resist any slippage between the outer surface and the bone surfaces in the joint. In addition to providing surface friction at the interface with the bone, the outer surfaces may be adapted to allow for bony ingrowth, which acts to further stabilize the plates or shells in place over time. The inner surfaces of the plates or shells are relatively smooth, and adapted to slide easily with low friction across a portion of the outer surface of an elastically deformable, resilient central body disposed between the plates or shells. Desirably, the inner surfaces have an average roughness of about 1 to about 8 microinches, more particularly less than about 3 microinches. The central body has a shape that cooperates with the shape of the inner surface of the plate or shell so as to provide motion similar to that provided by a healthy joint.

The surgical implant of the present embodiment provides exceptional stability, because the roughened outer surfaces of the plates or shells and their geometric shape supply sufficient frictional force to keep the implant from slipping from its proper position on the surfaces of the bones forming the joint. In addition, the geometry of the outer surfaces and the prepared surfaces of the bone cooperate to contain the implant between the bone surfaces. The smooth inner surfaces of the rigid opposing plates or shells are shaped to cooperate and articulate with the shape of the smooth surface of the deformable resilient central body to allow relatively unconstrained motion of the plates or shells with respect to the resilient central body until the limit of acceptable motion is reached. Once the limit of allowable motion is reached, the shape of the inner surface of the plate or shell cooperates with the shape of the deformable resilient central body to effectively resist any movement beyond the desired motion. This allows the motion of a joint containing the implant to closely approximate the motion provided in a healthy joint, alleviating undesirable stresses imposed on the joint or bone structure, or in the case of a vertebral implant, on adjacent joints as well. This, in turn, reduces the likelihood of further joint degeneration in adjacent joints.

The deformable resilient central body also provides elasticity and dampening properties, similar to those provided by healthy joint tissue. It is also sufficiently creep-resistant or resistant to plastic deformation to avoid post-operative loss of disc space height and to maintain appropriate joint geometry. The surface of the central body is hard, in some embodiments harder than the interior, which provides good wear resistance. It is also very lubricious, which provides good tribological properties in conjunction with the inner surfaces of the rigid plates or shells.

The resulting implant is safe because it can be implanted with precision, and once implanted, it is stable. It is extremely effective because the geometry of the internal surfaces is configured to provide a range of motion that closely approximates that provided by healthy joint tissue, thus allowing coordinated movement of the spine and reducing stress on adjacent joints.

In another embodiment an implant is provided that effectively provides an artificial diarthroidal-like joint, suitable for use in replacing any joint, but particularly suitable for use as an intervertebral disc endoprosthesis. In this aspect, the implant contains, in addition to the opposing rigid plates or shells and deformable, resilient central body described above, a flexible sleeve or sheath that extends between edges of the opposing plates or shells.

The inner surface of this sheath, together with the inner surfaces of the rigid plates or shells, defines a cavity surrounding the central body. Most, if not all, of the interior space of this cavity can be filled with a fluid lubricant, further decreasing the frictional force between inner surfaces of the plates or shell and the surface of the central body, again within the constraints of allowable motion.

The flexible sleeve or sheath serves to hold the implant together as a single unit, making it easier to manipulate during the implant procedure. It also retains the lubricant within the implant and provides a contained, sealed environment that keeps tissue from entering the interior of the implant, isolates the central body from possible attack or degradation by body fluids, and prevents any wear debris that might be generated from exiting the implant and migrating into surrounding tissues. The implant therefore provides a sealed capsule presenting only biocompatible surfaces to surrounding tissues, and keeping wear surfaces internal to the implant and permanently lubricated. The result is an implant with extremely good durability, because the articulating surfaces have been isolated away from the natural bone surfaces and placed in a lubricated capsule.

In yet another embodiment a vertebral endoprosthesis is provided having an upper and a lower rigid, opposed, biocompatible plate or shell. Each shell comprises an outer, rough surface, an inner, smooth surface, and an edge between the surfaces. The inner smooth surface of at least one of the plates or shells comprises a first motion limiting device. A deformable, resilient central body is disposed between the inner, smooth surfaces of the upper and lower plates or shells. The central body comprises a smooth upper surface adjacent to the inner smooth surface of the upper plate or shell and a smooth lower surface adjacent to the inner smooth surface of the lower plate or shell. A second motion limiting device is disposed on at least one of the smooth upper and lower surfaces and is adapted to contact the first motion limiting device and limit the relative motion of the plate or shell with respect to the central body.

The inner surfaces of the plates or shells can desirably be concave, and articulate with smooth upper surfaces of the deformable resilient central body that are convex. This arrangement creates, in effect, an artificial ball-and-socket-like joint in the intervertebral space, which joint is inherently stable under compression.

In a more specific embodiment, the vertebral endoprosthesis contains an upper and a lower rigid, opposed biocompatible concavo-convex shell. Each shell comprises an outer, rough convex surface, comprising a porous coating of a biocompatible material and an inner concave surface. The inner, concave surface comprises a smooth contact area and an axial post extending toward the opposing shell. An edge is disposed between the surfaces and comprises a circumferential groove adapted to receive a retaining ring and a first ridge circumscribing the contact area of the inner concave surface and extending axially toward the opposing shell. The edge further comprises an insertion tab extending axially away from the opposing shell, and comprising an opening adapted to releasably engage a tool for manipulating, inserting, or removing the endoprosthesis. The endoprosthesis has a closable passage between the outer surface and the inner surface of the shell.

A deformable, resilient central body is disposed between the inner, smooth concave surfaces of the upper and lower shells. The body has smooth convex upper and lower surfaces complementary and adjacent to the smooth contact area of the inner surfaces of the respective upper and lower shells. Furthermore, the body comprises a second ridge circumscribing each of the smooth convex upper and lower surfaces and adapted to contact the first ridge of the adjacent shell and limit the relative motion of the shell with respect to the central body. The body further comprises a laterally extending equatorial ridge disposed between the first ridge of the upper concavo-convex shell and the first ridge of the lower concavo-convex shell and an opening in the upper and lower convex contact surfaces adapted to receive the axial post of the inner surface of each shell.

An elastic sheath or sleeve is disposed between the upper and lower shells and surrounds the central body. The sheath comprises an inner surface, an outer surface, an upper edge secured to the upper shell, and a lower edge secured to the lower shell, wherein the inner surface of the sheath and the inner surfaces of the shells define an enclosing cavity.

An upper retaining ring of a biocompatible material is disposed in the circumferential groove in the upper concavo-convex shell and secures the upper edge of the elastic sheath or sleeve to the shell. A lower retaining ring of a biocompatible material is disposed in the circumferential groove of the lower concavo-convex shell and securing the lower edge of the sheath or sleeve to the shell.

This endoprosthesis provides the advantages described above and more specifically provides an implantable vertebral joint that approximates the disc height and range of motion of a healthy intervertebral disc, with significantly increased durability relative to natural intervertebral disc material, and without the drawbacks of spinal fusion.

In addition, the concavo-convex geometry of the opposing shells, and the precise preparation of a mating concave surface in the vertebral body endplates, into which the convex outer surfaces of the shells are inset, provide a highly stable implanted joint. Coupled with the roughness provided by the porous coating on the outer surface of the shell, this inset shape holds the implant firmly in place so that it cannot migrate and come into contact with nerves or blood vessels, and so that the desired bony ingrowth can occur. The convex outer surface also provides additional surface area that contacts cancellous bone, increasing both the opportunity for bony ingrowth and the frictional force holding the shells in place. The mating of the concave inner surfaces of the shells with the curved shape of the central body provides a simple ball-and-socket-like system that is inherently highly stable under compression, as it will be when implanted. The embodiment using concavo-convex shells and a convex surface on the deformable central body therefore provides immediate mechanical stability.

Because the range of motion provided by the implant closely approximates that of a healthy disc, post-operative adjacent level disc degeneration is minimized or avoided entirely. In addition, the implant does not significantly constrain joint torsion, but instead relies on the remaining soft tissue (e.g., remaining disc annulus, ligaments, etc.) in and around the implanted joint to provide appropriate torsional constraint. Neither the shapes of the plates or shells or of the central body, or of the central retaining posts or central axial opening restrict the torsional movement of the shells relative to the central body (i.e., the rotation of the shells or of the central body about a central axis). This is of benefit because it significantly decreases the stress imposed on the interface between the bone surfaces and the outer surfaces of the implant, making movement of these implant surfaces relative to the bone less likely. This, in turn, increases the likelihood of bony ingrowth instead of fibrous tissue formation, and therefore increases long-term stability.

In another embodiment an assembly for preparing a vertebral disc space to receive a prosthesis is provided. The assembly comprises a support frame that is adapted to attach to a plurality of vertebral bodies. A guide block having an opening disposed there through may operatively connect to the support frame. A position control mechanism may further be provided for controlling the position of the guide block relative to the support frame. A bone-removal device may be positioned through the opening of the guide block and operatively connect to the guide block. The bone-removal device may comprise a tool having a bone-removal element extending from the tool.

In yet another embodiment, an assembly for preparing a disc space for implantation of a prosthesis may comprise a sagittal wedge adapted to be disposed between a pair of vertebral bodies. A support frame and a disc spacer clip may be positioned over the sagittal wedge. A tilting guide member may be adapted to be positioned in the disc spacer clip. A transverse unit for mounting to the tilting guide member may be provided for accommodating a bone-removal tool.

BRIEF DESCRIPTION OF THE DRAWINGS

FIG. 19 is a schematic view of surgical instruments suitable for implanting an intervertebral endoprosthesis, such as that of FIG. 12.

FIG. 26 is a perspective schematic view of the support frame of FIG. 25 disposed over the sagittal wedge of FIG. 23, which is disposed between two vertebral bodies.

FIG. 27 is a perspective view of a disc spacer clip used in implanting an intervertebral endoprosthesis.

FIG. 28 is a schematic perspective view showing placement of the disc spacer clip of FIG. 27 relative to the support frame, sagittal wedge, and vertebral bodies.

FIG. 32 is a perspective view of a transverse unit used in implanting the intervertebral endoprosthesis. FIG. 32A is a perspective view of the entire transverse unit, while FIG. 32B is a close-up perspective view of an assembly of a central member and inner member of the transverse unit.

FIG. 37 is a schematic perspective view showing the arrangment of the bone removal device and transverse unit, as well as pivot tool 396.

FIG. 38 is a schematic perspective view of two embodiments of intervertebral endoprostheses. FIG. 38A shows an intervertebral endoprosthesis having a more rounded shape, while FIG. 38B shows an intervertebral endoprosthesis having a more rectilinear shape.

Figure 1:
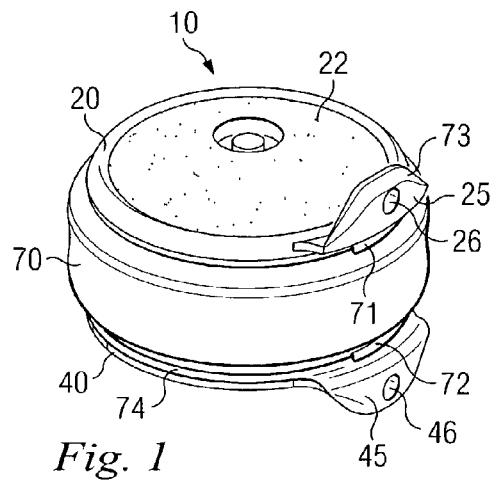
FIG. 1 is a perspective drawing of an intervertebral endoprosthesis in accordance with one embodiment.
Figure 3:
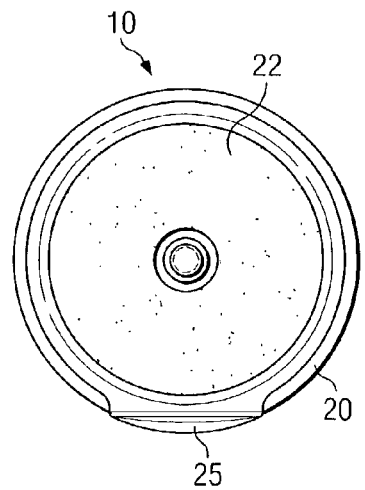
FIG. 3 is a top plan view of the intervertebral endoprosthesis shown in FIGS. 1 and 2.
Figure 2:
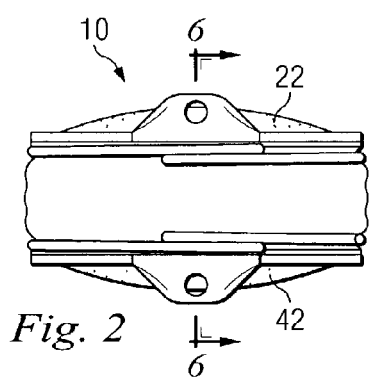
FIG. 2 is an elevational view of the intervertebral endoprosthesis shown in FIG. 1.

The invention can be more clearly understood by reference to some of its specific embodiments, described in detail below, which description is not intended to limit the scope of the claims in any way.

DETAILED DESCRIPTION

In general, a prosthetic device is provided for replacing a human bone joint and instrumentation designed to facilitate the precise positioning of the device within the joint.

In broad aspect, the size and shape of the implant are substantially variable, and this variation will depend upon the joint geometry. Moreover, implants of a particular shape can be produced in a range of sizes, so that a surgeon can select the appropriate size prior to or during surgery, depending upon his assessment of the joint geometry of the patient, typically made by assessing the joint using CT, MRI, fluoroscopy, or other imaging techniques.

The rigid opposing plates or shells can be made of any rigid, biocompatible material, but are generally made of a biocompatible metal, such as stainless steel, cobalt chrome, ceramics, such as those including $Al_2O_3$ or $Zr_2O_3$, or titanium alloy. ASTM F-136 titanium alloy has been found to be particularly suitable. As indicated above, the outer surface of the rigid opposing plates or shells are rough, in order to restrict motion of the shells relative to the bone surfaces that are in contact with the plates. This is particularly important in the time period just after implantation (the "acute" phase of healing), since excessive movement of the implant relative to the bone can result in the formation of fibrous tissue between the bone and the implant, rather than the bony ingrowth, which is desirable for long term implant stability (i.e., during the "chronic" phase of healing). It has been discovered that a porous coating formed from non-spherical sintered beads provides very high friction between the outer surface of the shell and the bone, as well as providing an excellent interaction with the cancellous bone of the joint, increasing the chances of bony ingrowth. One example of a suitable nonspherical sintered bead coating is that made of pure titanium, such as ASTM F-67. The coating can be formed by vacuum sintering.

At least a portion of the inner surface of each plate or shell is smooth, and of a shape that complements and articulates with the shape of at least a portion of the central body. This smoothness and correspondence in shape provides unconstrained movement of the plate or shell relative to the central body, provided that this movement occurs within the allowable range of motion.

The structural features of the shapes of the inner surface of the plate or shell and the central body that interact to limit the movement to this allowable range will necessarily vary to some extent, based on the joint in which the implant will be used. As an example, the edge of the plate or shell can be extended toward the central body, so as to form a wall that, under shear, can contact a ridge or shoulder formed in the surface of the central body. This will allow for unconstrained motion of the plate or shell except in a direction that will bring the extension into contact with the ridge. By forming the extension around the entire edge of the shell, and by forming a ridge or shoulder that encloses a portion of the surface of the central body, translational, flexural, extensional, and lateral motion of the plate or shell relative to the central body can be constrained in all directions. Those of skill in the art will recognize that a bead or ridge at other locations on the inner surface of the plate or shell will serve a similar purpose, and that the location of this bead or ridge, as well as the ridge or stop on the central body, can be varied between implants for different joints, in order to obtain the desired range of motion for that particular joint.

The plates may be identical, which is desirable for ease of manufacture, or may be of different design (shape, size, and/or materials) to achieve different mechanical results. For example, differing plate or shell sizes may be used to more closely tailor the implant to a patient's anatomy, or to shift the center of rotation in the cephalad or caudal direction.

In a more particular embodiment, the inner surface of the shell and the outer surface of the central body can contain complementary structures that will function as an expulsion stop, so that the central body cannot be expelled from between the opposing plates or shells when the plates or shells are at maximum range of motion in flexion/extension. Examples of such structures include a post and corresponding hole to receive the post. The hole can have a diameter sufficiently large that relative motion between the shells and central body is unconstrained within the allowable range of motion, but that will nevertheless cause the post to arrest the central body before it is expelled from the implant under extreme compression. Alternatively, the diameter of the post may be such that it limits the translational movement of the central body during normal motion of the spine by contacting the surface of the hole in the central body at the limit of the allowable range of motion for the device.

The elastically deformable, resilient central body may also vary somewhat in shape, size, composition, and physical properties, depending upon the particular joint for which the implant is intended. The shape of the central body should complement that of the inner surface of the shell to allow for a range of translational, flexural, extensional, and rotational motion, and lateral bending appropriate to the particular joint being replaced. The thickness and physical properties of the central body should provide for the desired degree of elasticity or damping. Accordingly, an elastomeric material is typically used for the central body. However, the central body should be sufficiently stiff to effectively cooperate with the shell surfaces to limit motion beyond the allowable range. The surface of the central body should be sufficiently hard to provide acceptable wear characteristics. One way to achieve this combination of properties is to prepare a central body having surface regions that are harder than the material of the central body closer to its core. The central body is therefore desirably a biocompatible elastomeric material having a hardened surface. Polyurethane-containing elastomeric copolymers, such as polycarbonate-polyurethane elastomeric copolymers and polyether-polyurethane elastomeric copolymers, generally having durometer ranging from about 80A to about 65D (based upon raw, unmolded resin) have been found to be particularly suitable for vertebral applications. If desired, these materials may be coated or impregnated with substances to increase their hardness or lubricity, or both. Examples of suitable materials are provided in more detail below.

The shape of the central body may also be designed to prevent contact between the edges of the rigid opposing shells during extreme motion of the implant. For example, a ridge or lip in the region of the central body between the shells and extending laterally can provide a buffer, preventing contact between the shells. This prevents friction and wear between the shells, thereby avoiding the production of particulates, which could cause increased wear on the internal surfaces of the implant.

In a particular embodiment, one or both of the rigid opposing shells can be provided with an opening therein, in the form of a passage between the outer and inner surfaces. When the implant is partially assembled, i.e., the deformable resilient central body has been disposed between the rigid opposing shells, and the sheath has been attached to the edges of the shells, the passage can be used to introduce liquid lubricant into the implant. The passage can then be closed off (e.g., by filling it with an appropriately sized plug), thereby providing a sealed, lubricant filled inner cavity.

Attachment of the sheath to the rigid, opposing shells can be accomplished in a variety of ways. Typically the rigid opposing shell is made from a biocompatible metallic alloy, e.g., a titanium alloy, while the sheath is typically made from an elastomeric polymeric material, such as segmented polyurethane. Attachment of the sheath to the shell can be accomplished by providing the edge of the rigid shell with a circumferential groove (the term "circumferential" in this context does not imply any particular geometry). The groove is of a shape and depth sufficient to accept a retaining ring, typically made of a biocompatible weldable wire, such as stainless steel or titanium. The sheath can be disposed so that it overlaps the circumferential groove, and the retaining ring formed by wrapping the wire around the groove over the overlapping portion of the sheath, cutting the wire to the appropriate size, and welding the ends of the wire to form a ring. Laser welding has been found to be particularly suitable in this regard.

The embodiment as described above can be used as a prosthetic implant in a wide variety of joints, including hips, knees, shoulders, etc. The description below focuses on an embodiment wherein the implant is a spinal disc endoprosthesis, but similar principles apply to adapt the implant for use in other joints. Those of skill in the art will readily appreciate that the particulars of the internal geometry will likely require modification from the description below to prepare an implant for use in other joints. However, the concept of using a core body having geometric features adapted to interact with inner surfaces of opposing shells to provide relatively unconstrained movement of the respective surfaces until the allowable range of motion has been reached, and the concept of encasing these surfaces in a fluid filled capsule formed by the opposing shells and a flexible sheath, are applicable to use in any joint implant.

Figure 4:
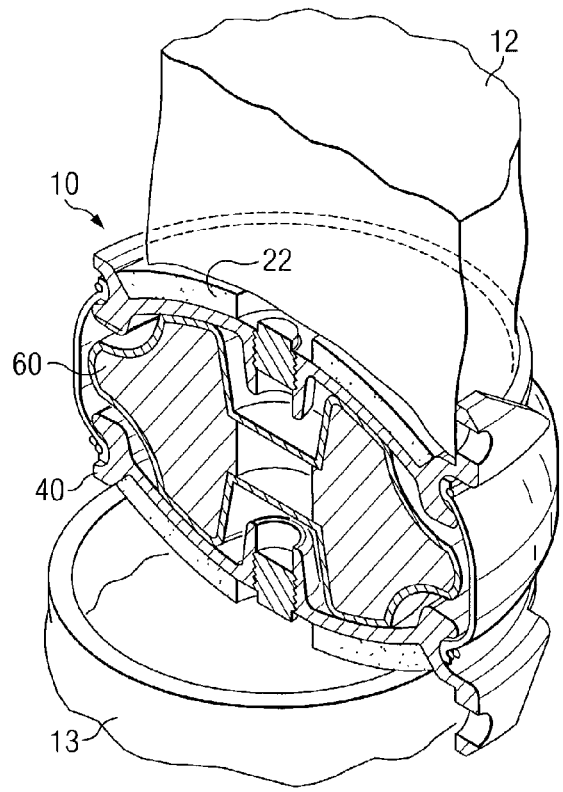
FIG. 4 is an isometric cross sectional view of the intervertebral endoprosthesis shown in FIGS. 1, 2, and 3.
Figure 6:
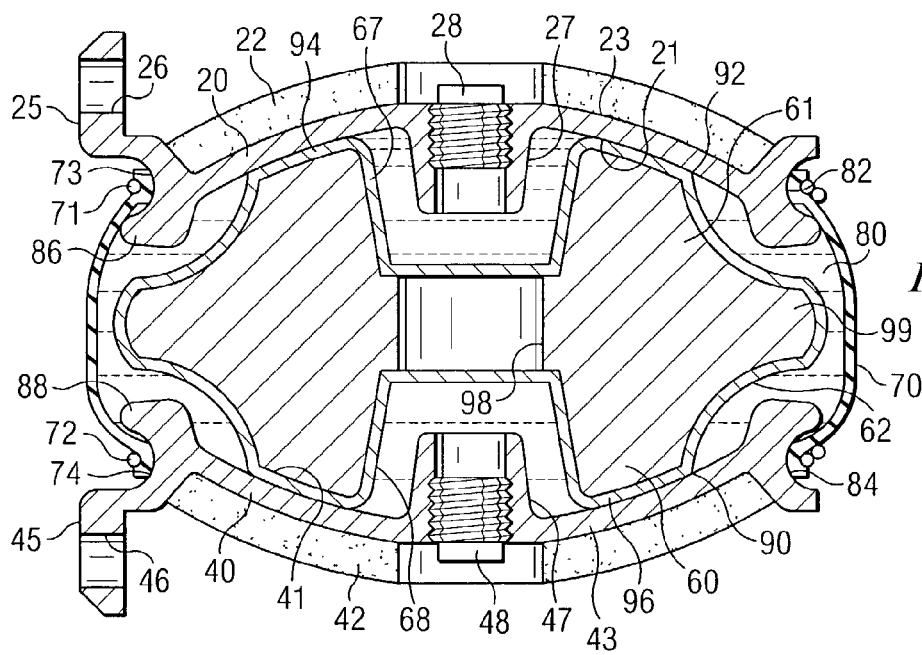
FIG. 6 is a sectional view of the intervertebral endoprosthesis shown in FIGS. 1–4.

Reference is made below to the drawings, which shall now be used to illustrate a specific embodiment, namely a spinal disc endoprosthesis. As can be seen best in the exploded view shown in FIG. 7, in accordance with this preferred embodiment, the implant includes four main components: two shells 20, 40, a central body 60, and a sheath 70. The complete assembly of the device is shown in FIGS. 4 and 6, wherein the central body 60 is bracketed between shells 20, 40. The flexible sheath 70 extends between the two opposing shells 20, 40, and encapsulates the central body 60. As described in further detail below, the geometric configuration of the shells 20, 40, the central body 60, and the sheath 70, are complementary. As such the geometric configuration of these components cooperate to (1) join the components into a unitary structure, and (2) define important functional features of the device.

Preferably, shells 20, 40 are cup-like so as to include an outer convex surface 23 and an inner concave surface 21, 41. The outer surfaces 23 can be coated with a nonspherical sintered bead coating 22, 42, or with some other coating that will promote bony ingrowth. The inner surfaces 21, 41 (shown in FIG. 6) are preferably very smooth, and may be machined or polished.

The shells 20, 40 include a number of geometric features that as described in further detail below cooperate with other components of the devices. Specifically, these features include a central retaining post 27, 47, an outer circumferential groove 82, 84, and a radial stop or an extension 86, 88. The central retaining post 27, 47 extends axially from inner surfaces 21, 41. In addition, each shell 20, 40 includes an edge 73, 74, respectively. The outer circumferential grooves 82, 84 extend into the edges 73, 74 of the shells 20, 40. As seen best in FIG. 6, the radial stops or extensions 86, 88 extend from the edges 73, 74 in a direction generally perpendicular to the general plane of the shells 20, 40.

Each shell 20, 40 may also be provided with tabs or flanges 25, 45. The tabs or flanges 25, 45 extend from a portion of the edges 73, 74 in a direction generally perpendicular to the general plane of the shells 20, 40, but in a direction generally opposite the radial stops or extensions 86, 88. The tabs or flanges 25, 45 help to prevent long-term migration within the disc space, as well as catastrophic posterior expulsion, and the resulting damage to the spinal cord, other nerves, or vascular structures. The tabs or flanges 25, 45 may contain openings 26, 46 that can releasably engage an insertion tool (not shown). The insertion tool will generally contain flexible prongs to releasably engage openings 26, 46. The insertion tool will also generally include a disengagement block that can press against the side of the implant once it has been properly positioned in the intervertebral space and force the openings 26, 46 off of the prongs of the tool. The shells 20, 40 can be made from any suitable biocompatible rigid material. In accordance with a preferred embodiment, the shells 20, 40 are made from a titanium alloy, and most preferably the titanium alloy is ASTM F-136. The bead coating 22, 42, however, is preferably made from ASTM F-67 pure titanium.

Figure 7:
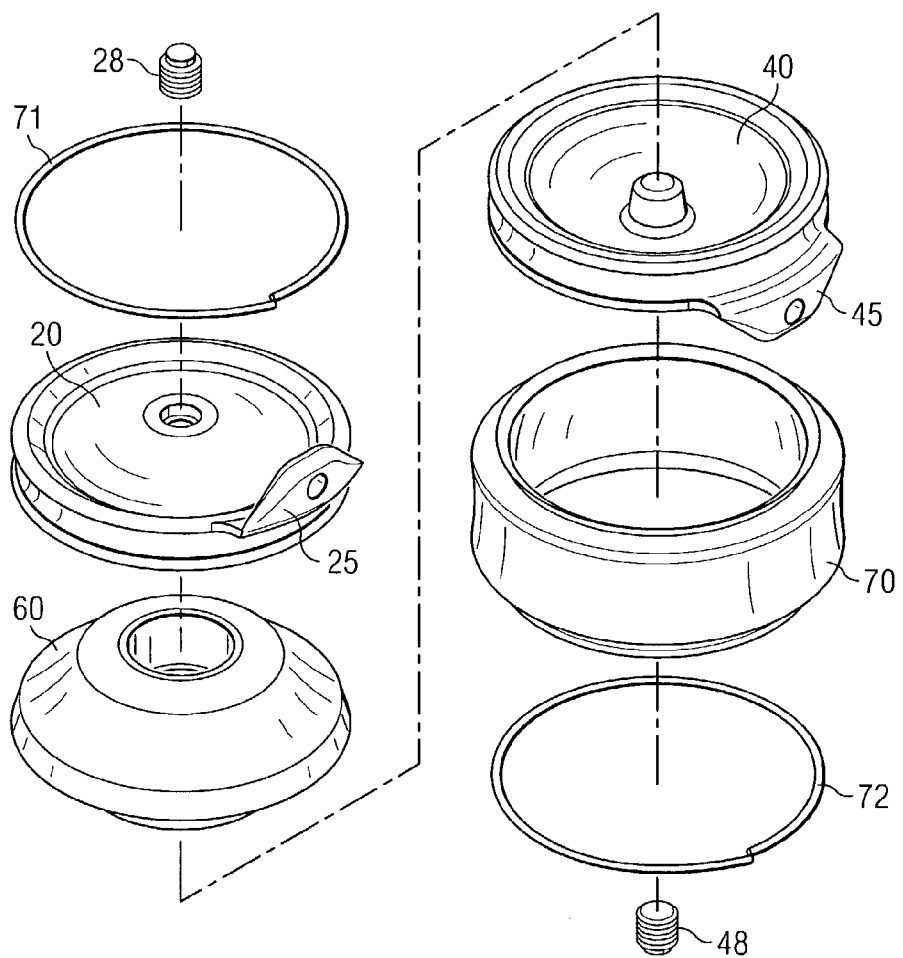
FIG. 7 is an exploded perspective view of the intervertebral endoprosthesis shown in FIGS. 1–4 and 6.
Figure 8A:
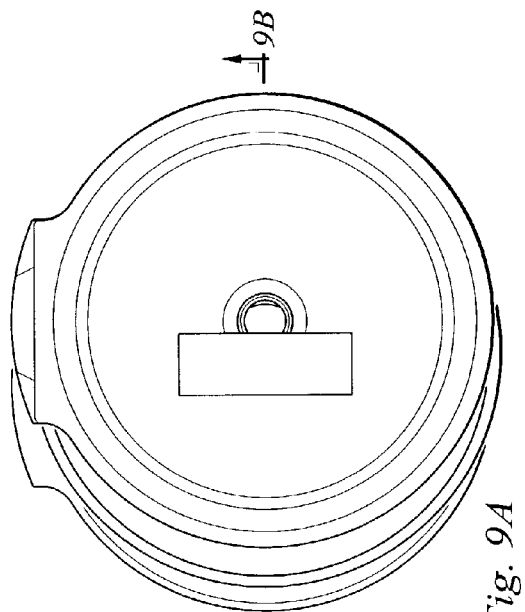
FIG. 8 is a plan view (A) and sectional view (B) of one embodiment of an intervertebral endoprosthesis undergoing lateral bending.
Figure 9A:
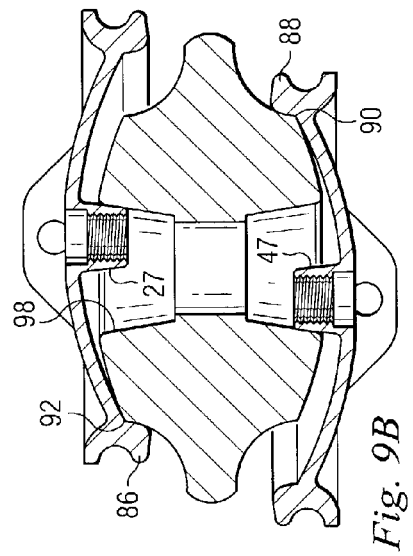
FIG. 9 is a plan view (A) and sectional view (B) of one embodiment of an intervertebral endoprosthesis undergoing translation.
Figure 8B:
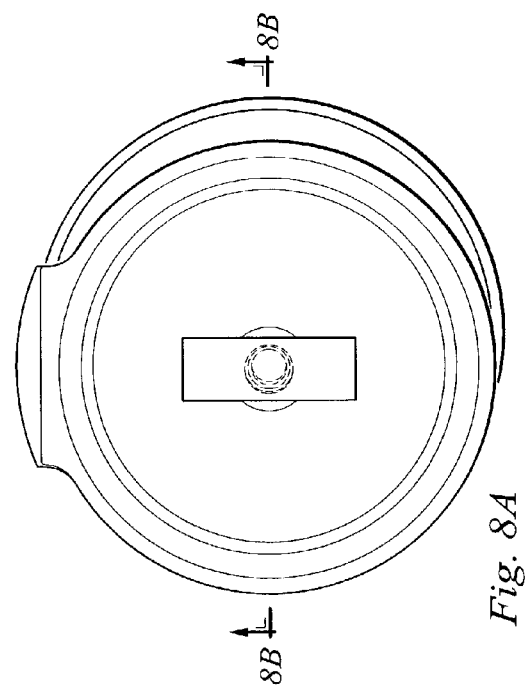
Figure 9B:
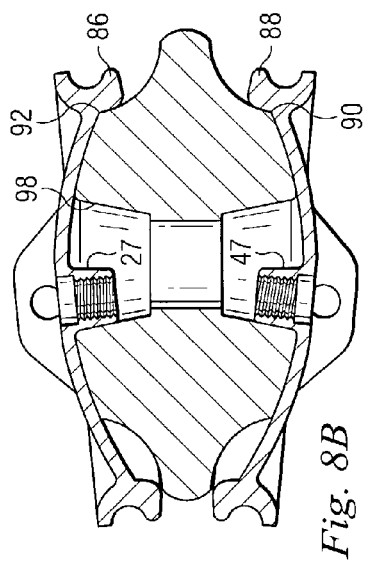

As shown best in FIG. 7, central body 60 is preferably a donut-shaped structure, and includes a convex upper contact surface 94, a convex lower contact surface 96, and a central axial opening 98 formed through an inner surface 67 of the central body. In addition, central body member 60 preferably includes an upper shoulder 92 and a lower shoulder 90. Each shoulder 90, 92 consists of an indentation in the surface of the central body member which defines a ledge that extends around the circumference of the central body 60.

The central body 60 is both deformable and resilient, and is composed of a material that has surface regions that are harder than the interior region. This allows the central body to be sufficiently deformable and resilient that the implant functions effectively to provide resistance to compression and to provide dampening, while still providing adequate surface durability and wear resistance. In addition, the material of the central body has surfaces that are very lubricious, in order to decrease friction between the central body and the rigid opposing shells.

The material used to make the central body is typically a slightly elastomeric biocompatible polymeric material, which may be coated or impregnated to increase surface hardness, or lubricity, or both, as described above. Coating may be done by any suitable technique, such as dip coating, and the coating solution may include one or more polymers, including those described below for the central body. The coating polymer may be the same as or different from the polymer used to form the central body, and may have a different durometer from that used in the central body. Typical coating thickness is greater than about 1 mil, more particularly from about 2 mil to about 5 mil. Examples of suitable materials include polyurethanes, such as polycarbonates and polyethers, such as Chronothane P 75A or P 55D (P-eth-PU aromatic, CT Biomaterials); Chronoflex C 55D, C 65D, C 80A, or C 93A (PC-PU aromatic, CT Biomaterials); Elast-Eon II 80A (Si-PU aromatic, Elastomedic); Bionate 55D/S or 80A-80A/S (PC-PU aromatic with S-SME, PTG); CarboSil-10 90A (PC-Si-PU aromatic, PTG); Tecothane TT-1055D or TT-1065D (P-eth-PU aromatic, Thermedics); Tecoflex EG-93A (P-eth-PU aliphatic, Thermedics); and Carbothane PC 3585A or PC 3555D (PC-PU aliphatic, Thermedics).

The last main component of this embodiment is the sheath 70. As show in FIG. 7, the sheath 70 is a tubular structure, and is made from a flexible material. The material used to make the sheath is typically biocompatible and elastic, such as a segmented polyurethane, having a thickness ranging from about 5 to about 30 mils, more particularly about 10–11 mils. Examples of suitable materials include BIOSPAN-S (aromatic polyetherurethaneurea with surface modified end groups, Polymer Technology Group), CHRONOFLEX AR/LT (aromatic polycarbonate polyurethane with low-tack properties, CardioTech International), CHRONOTHANE B (aromatic polyether polyurethane, CardioTech International), CARBOTHANE PC (aliphatic polycarbonate polyurethane, Thermedics).

As noted above, the various geometric features of the main components of this embodiment cooperate to join the components into a unitary structure. In general, the ends of the sheath 70 are attached to the shells, and the central body 60 is encapsulated between the shells 20, 40 and the sheath 70. More specifically, referring to FIG. 6, preferably the edges of flexible sheath 70 can overlap the outer circumferential grooves 82, 84 of the shells 20, 40. Retaining rings 71, 72 are then placed over the edges of the sheath 70 and into the circumferential grooves 82, 84, thereby holding the flexible sheath in place and attaching it to the shells. While any suitable biocompatible material can be used for the retaining rings, titanium or titanium alloys have been found to be particularly suitable. The retaining rings are desirably fixed in place by, e.g., welding the areas of overlap between the ends of the retaining rings. Because of the high temperatures needed to weld titanium and titanium alloys, and because of the proximity of the weld area to both the flexible sheath 70 and the central body 60, laser welding is typically used.

As also noted above, the various geometric features of the main components of this embodiment cooperate to define important functional features of the device. These features primarily include defining the kinematics of motion provided by the device, prohibiting expulsion of the central body 60, providing post assembly access to the interior of the device, providing an attachment mechanism for inserting the device, and providing a port for the insertion of lubricant into the implant cavity.

The kinematics of the motion provided by the prosthesis are defined primarily by the geometric interaction of the central body 60 and the shells 20, 40. Although the central body is encapsulated within the sheath and the shells, it is not attached to these components. Accordingly, the central body 60 freely moves within enclosed structure and is only constrained by geometric limitations. As seen best in FIG. 6, the concave shape of the inner surfaces 21, 41 of shells 20, 40 complements the convex surfaces 94, 96 of central body 60. As the shells 20, 40 glide across the convex surfaces 94, 96, relatively unconstrained translational, flexural, or extensional motion of shells 20, 40 with respect to central body 60 is achieved. When the desired limit of the range of motion is reached, extensions 86, 88 on shells 20, 40 are designed to contact shoulders 90, 92 on the central body 60. Specifically, the inner portion of the extension forms a circumferential ridge that limits the range of motion of the shells 20, 40 relative to the central body 60 by contacting central body shoulders 90, 92 at the end of the allowable range of motion. In an actual vertebral joint, this occurs at a joint flexion/extension of about ±10°, at lateral bending of about 11°, and/or at translation of about 2–3 mm.

As explained above, in one embodiment, the shells are concavo-convex, and their inner surfaces mated and articulated with a convex outer surface of the deformable resilient central body. The implant also contains a sheath or sleeve that is secured to the rims of the shells with retaining rings, and which, together with the inner surfaces of the shells, forms an implant cavity. In a particular aspect of this embodiment, using a coordinate system wherein the geometrical center of the implant is located at the origin, and assigning the x-axis to the anterior (positive) and posterior (negative) aspect of the implant, the y-axis to the right (positive) and left (negative) aspect of the implant, and the z-axis to the cephalad (positive) and caudal (negative) aspects of the implant, the convex portion of the outer surface and the concave portion of the inner surface of the shells can be described as a quadric surfaces, such that $$\frac{x^2}{a^2} + \frac{y^2}{b^2} + \frac{z^2}{c^2} = 1$$

where (±a,0,0), (0,±b,0), and (0,0,±c) represent the x, y, and z intercepts of the surfaces, respectively. Typical magnitudes for a, b, and c are about 11 mm, 30 mm, and 10 mm, respectively.

The implant is symmetrical about the x–y plane, and is intended to be implanted in the right-left center of the disc space, but may or may not be centered in the anterior-posterior direction. In any event, the implant is not allowed to protrude in the posterior direction past the posterior margin of the vertebral body.

As noted above, geometric features also serve to prevent the expulsion of the central body 60. In particular, this is achieved by the geometric interaction of the shells 20, 40 and the central body 60. Shells 20, 40 also contain central retaining posts 27, 47 which extend axially from inner surfaces 21, 41 into a central axial opening 98 in central body 60 and which stop central body 60 from being expelled from the implant during extreme flexion or extension. The diameter of central axial opening 98 is somewhat larger than the diameter of central retaining posts 27, 47. In the coordinate system described above, the central axis of the retaining posts 27, 47 is typically coincident with the z-axis, but may move slightly to accommodate various clinical scenarios. The shape of the posts 27, 47 may be any quadric surface. However, a truncated tapered elliptical cone is a particularly suitable geometry. Similarly, the geometry of the central axial opening 98 of the central body 60 will correspond to the geometry of the retaining posts 27, 47, and will have a similar geometry.

Also described above, the shells 20, 40 contain extensions or walls 86, 88 formed on the inner surface 21, 41, for example around the edge of the shell, and that extend toward the deformable resilient central body 60. This extension or wall 86, 88 limits allowable translation of the deformable resilient central body 60 with respect to the shell when the extension comes into contact with the shoulder 90, 92 formed on the surface of the central body, e.g., under shear loading of the implant. The height of the extension or wall 86, 88 should be less than about 2.5 mm in order to allow the full range of desired flexion/extension and right/left lateral bending motions.

The resilient deformable central body 60 contains surfaces that are described by an equation similar to that for the inner surfaces 21, 41 of the shells, and which articulates with those inner surfaces. The central body 60 will have a plane of symmetry if identical opposing shells 20, 40 are used. As described above, the central body 60 also features an equatorial ridge 99 that acts as a "soft stop" in the event the patient participates in extreme activities that result in movements greater than the designed range of flexion/extension or lateral bending. In such a situation, the central body 60 will have translated until the retaining post 27, 47 has contacted the inner surface of the central axial opening 98, and the extension or wall 86, 88 will have contacted the shoulder of the central body. Opposite the wall/shoulder contact, the edges of the shells will be in close proximity, but will be kept from contacting each other by contact with the equatorial ridge 99 of the central body. If desired, the thickness of the ridge 99 can be varied to further limit the range of motion.

Another important characteristic of this embodiment is the provision of a means for accessing the interior of the device after it has been assembled into a unitary structure. This means consists of a central axial opening included in the shells 20, 40. Typically, this opening will be provided through central retaining posts 27, 47. By providing access to the interior of the device, sterilization can be done just prior to implantation of the device. Sterilization is preferably accomplished by introducing an ethylene oxide surface sterilant. Caution should be exercised in using irradiation sterilization, as this can result in degradation of the polymeric materials in the sheath 70 or central body 60, particularly if these include polyurethanes.

Figure 5:
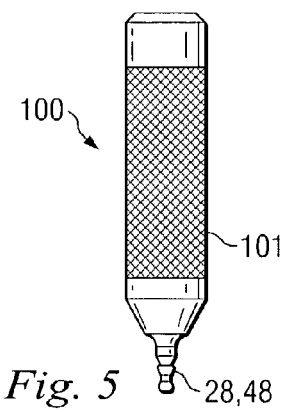
FIG. 5 is a plan view of an implant plug and plug installation tool used to insert a plug into an intervertebral endoprosthesis.

After sterilization, the central openings can be sealed using plugs 28, 48. Preferably, only one plug is inserted first. The plug is inserted using insertion tool 100, shown in FIG. 5, and which contains handle 101 and detachable integral plug 28, 48. The tool 100 is designed so that plug 28, 48 detaches from the tool when a predetermined torque has been reached during insertion of the plug. The tool 100 can then be discarded.

After one plug has been inserted into one of the shells, a lubricant 80 is preferably introduced into the interior of the device prior to inserting the second plug. To do this a syringe is used to introduce the lubricant into the remaining central opening, and the implant is slightly compressed to remove some of the excess air. Another insertion tool 100 is then used to insert a plug into that central opening, thereby completely sealing the interior of the device from its exterior environment. In accordance with one embodiment the lubricant 80 is saline. However, other lubricants may be used, for example, hyaluronic acid, mineral oil, and the like.

The two shells 20, 40 are virtually identical in shape and composition, however those of skill in the art will understand that it is possible to use shells of different sizes (including thicknesses), shapes, or materials, e.g., in order to provide a more customized fit to the patient's anatomy.

The deformable resilient central body 60 is disposed between the opposed shells, as described above and illustrated in the drawing figures. Its upper and lower surfaces articulate with the upper and lower shells, respectively, and have a geometry that is similar to that of the shells.

Figure 10A:
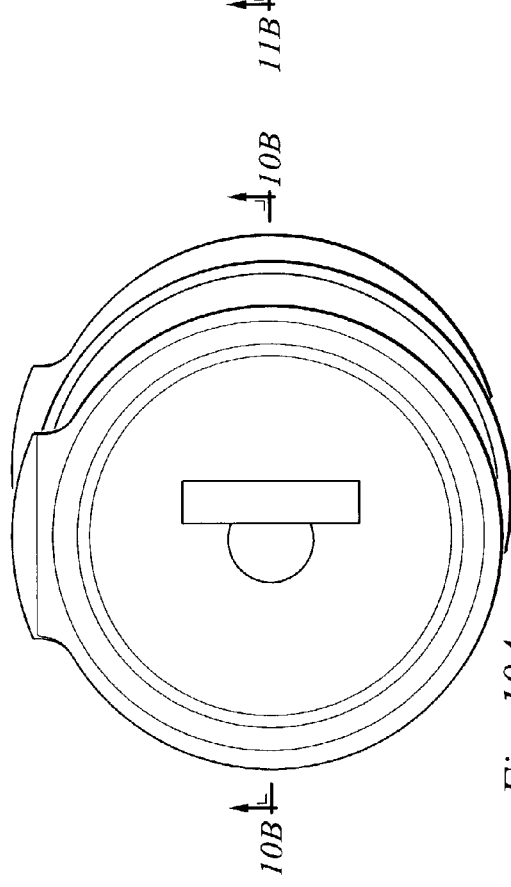
FIG. 10 is a plan view (A) and sectional view (B) of one embodiment of an intervertebral endoprosthesis undergoing lateral bending.
Figure 10B:
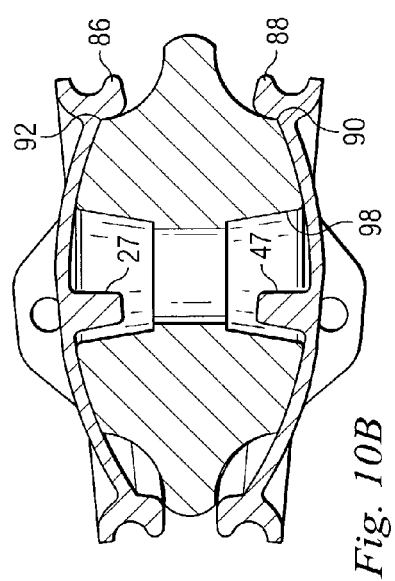
Figure 11A:
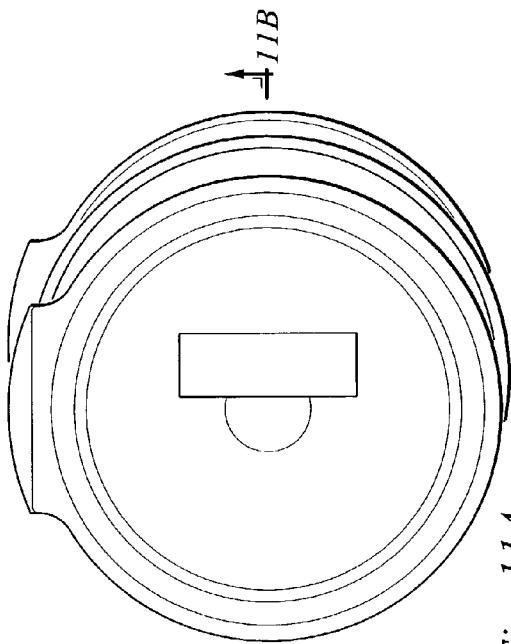
FIG. 11 is a plan view (A) and sectional view (B) of one embodiment of an intervertebral endoprosthesis undergoing translation.
Figure 11B:
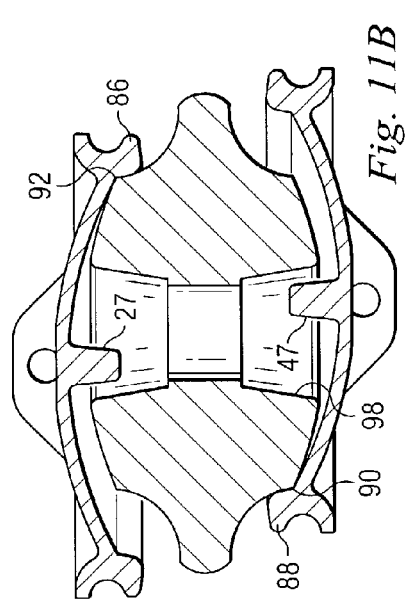

The kinematics of various embodiments of the implant are illustrated in FIGS. 8, 9, 10, 11. FIG. 8A illustrates a plan view of an implant having a hollow central retaining post and undergoing lateral bending. The range of lateral bending is limited to about 11°, such as in FIG. 8B, which is a sectional view along line 8B—8B of FIG. 8A. Contact of the walls or extensions 86, 88 of the shells with shoulders 90, 92 of the central body limit the range of motion to that desired. The central retaining posts 27, 47 may also contribute to limiting the range of motion by contact with the central axial opening 98 of the central body. FIG. 9A illustrates a plan view of an implant of the type shown in FIG. 8 undergoing lateral translation. FIG. 9B shows a sectional view along line 9B—9B. Again, the contact between walls or extensions 86, 88 of the shells and shoulders 90, 92 of the central body limit the range of motion to that desired, and central retaining posts 27, 47 may also contribute to limiting the range of motion. FIGS. 10 and 11 provide similar plan and sectional views (along line 10B—10B and 11B—11B, respectively), illustrating a different embodiment of the implant (without a hollow central retaining post) undergoing lateral bending (FIG. 10) and lateral translation (FIG. 11). In each case, the range of motion is limited by contact between walls or extensions 86, 88 of the shells and shoulders 90, 92 of the central body.

As described above, the implant is desirably used as an endoprosthesis inserted between two adjacent vertebral bodies. The implant may be introduced using a posterior or anterior approach. For cervical implantation, an anterior approach is preferred. The implanting procedure is carried out after discectomy, as an alternative to spinal fusion. The appropriate size of the implant for a particular patient, determination of the appropriate location of the implant in the intervertebral space, and implantation are all desirably accomplished using precision stereotactic techniques, apparatus, and procedures, such as the techniques and procedures described in copending U.S. Ser. No. 09/923,891, filed on Aug. 7, 2001, the entire contents of which are hereby incorporated by reference. Of course, non-stereotactic techniques can also be used. In either case, discectomy is used to remove degenerated, diseased disc material and to provide access to the intervertebral space. This access is used to remove a portion of the vertebral body using a burr or other appropriate instruments, in order to provide access to the intervertebral space for a transverse milling device of the type described in U.S. Ser. No. 08/944,234, the entire contents of which are hereby incorporated by reference. The milling device is used to mill the surfaces of the superior and inferior vertebral bodies that partially define the intervertebral space to create an insertion cavity having surfaces that (a) complement the outer surfaces of the implant and (b) contain exposed cancellous bone. This provides for an appropriate fit of the implant with limited motion during the acute phase of implantation, thereby limiting the opportunity for fibrous tissue formation, and increases the likelihood for bony ingrowth, thereby increasing long-term stability.

Figure 12:
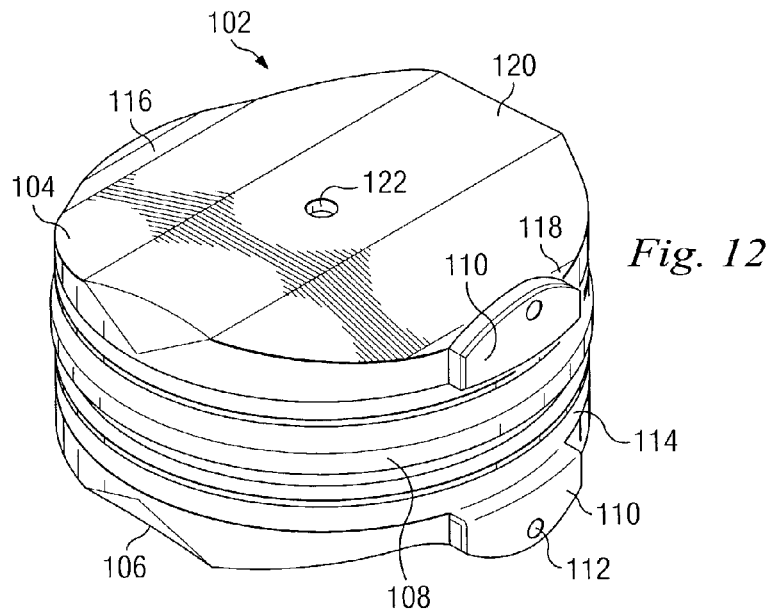
FIG. 12 is a perspective view of one embodiment of an intervertebral endoprosthesis, particularly suitable for lumbar use.

Referring now to FIG. 12, an alternative embodiment of a human joint prosthesis 102 is provided. Prosthesis 102 is particularly adapted for replacing a spinal disc, and in particular a lumbar spinal disc. Prosthesis 102 includes an upper member 104, a lower member 106, and a central member 108. The upper member 104 and lower member 106 may include an anterior wing 110, as illustrated in FIG. 12. Alternatively, the anterior wings may be excluded from the device. If an anterior wing is included, it may include anterior wing opening 112 to facilitate attaching the device to an insertion or removal tool. The upper member 104 and lower member 106 may also include a circumferential groove 114. Circumferential groove 114 is adapted to receive a retaining ring (not shown) which would secure a sheath (not shown) to the upper and lower members as shown in the embodiment illustrated in FIG. 1.

The upper and lower members 104, 106 preferably include an outer surface having a posterior stabilizing flat 116, an anterior stabilizing flat 118, and an outer surface 120 extending therebetween. As is described in greater detail herein below, posterior stabilizing flat 116 and anterior stabilizing flat 118 provide a means for preventing rotation of the device about its anterior-posterior axis. In addition, upper and lower members 104, 106 many also include interior access port 122. Interior access port 122 provides a means for introducing a lubricant into the interior of the device.

Figure 13:
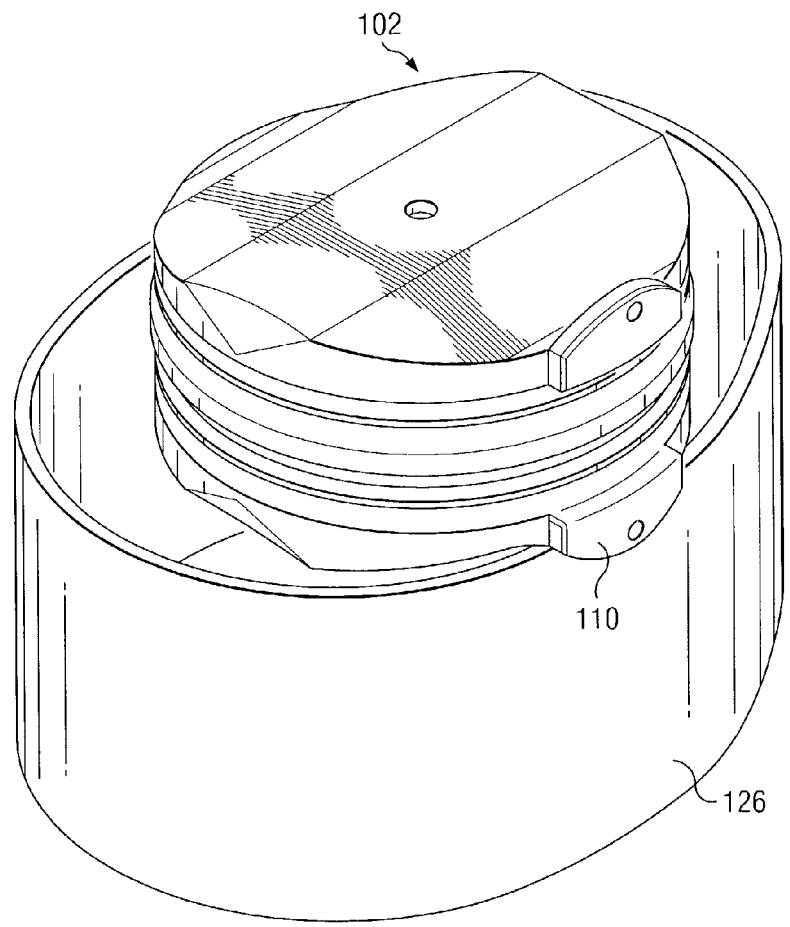
FIG. 13 is an anterior-posterior cross-sectional schematic view of the intervertebral endoprosthesis of FIG. 12.

FIG. 13 provides a schematic perspective view of the implanted endoprosthesis with one of the vertebral bodies cut away to show the arrangement of the endoprosthesis with the remaining vertebral body 126. As shown, the endoprosthesis 102 is implanted such that anterior wing 110 adjoins the anterior surface of the vertebral body.

Figure 14:
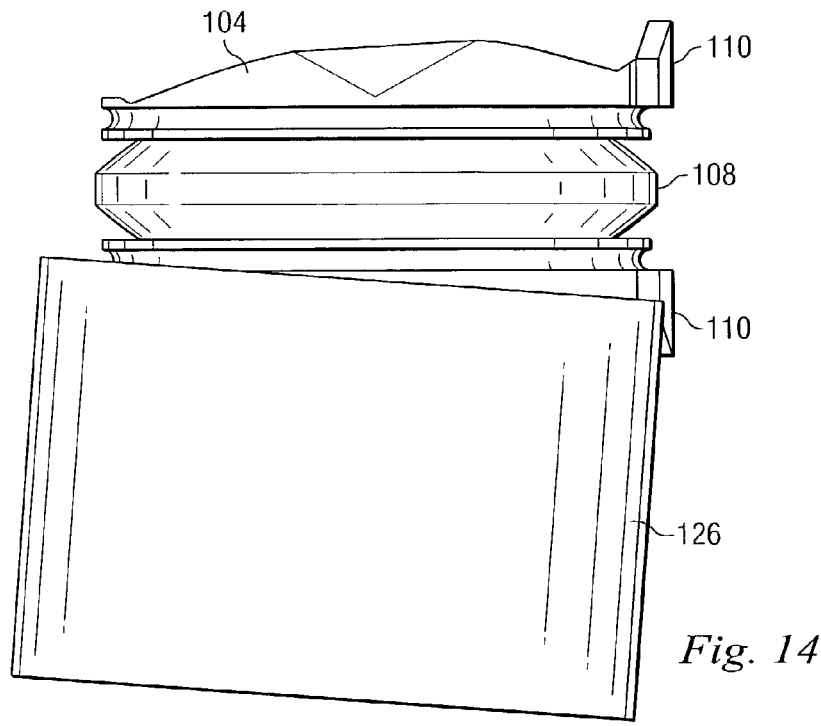
FIG. 14 is a side perspective view of the implanted endoprosthesis corresponding to FIG. 13.

FIG. 14 is a side perspective view of the implanted endoprosthesis corresponding to FIG. 13. The anterior-posterior angulation of the endoprosthesis in its prepared cavity relative to the surface of the vertebral body endplate is apparent.

Figure 15:
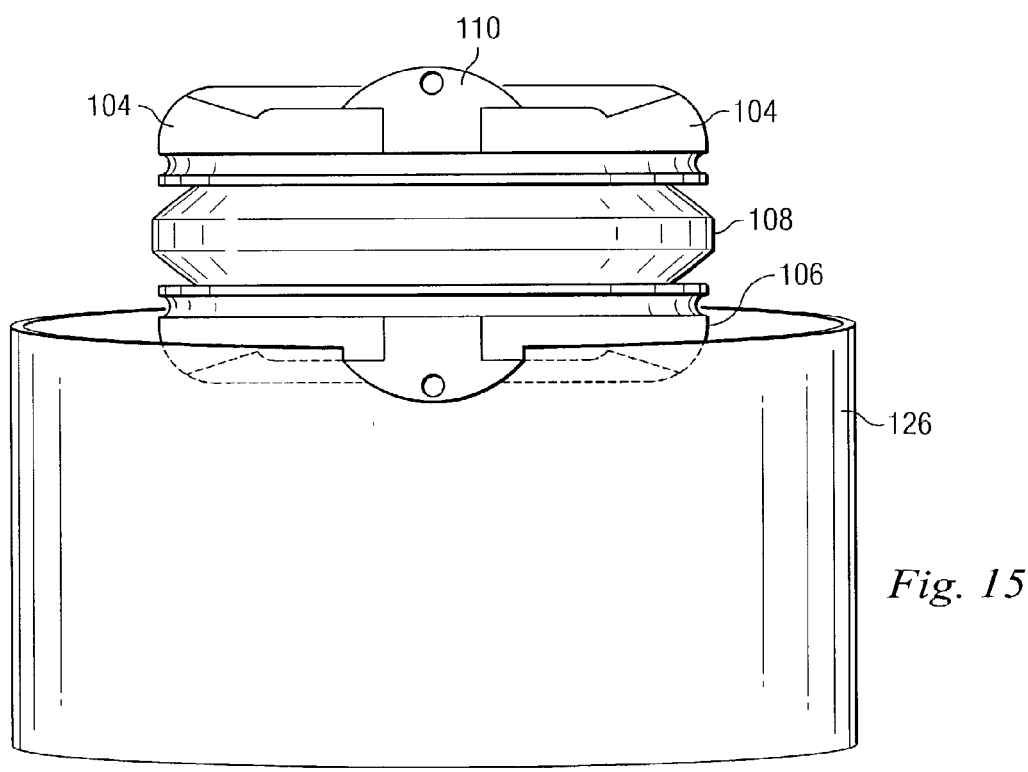
FIG. 15 is a front schematic view of the implanted endoprosthesis with one of the vertebral bodies cut away.

FIG. 15 is a front schematic view of the implanted endoprosthesis with one of the vertebral bodies cut away.

Figure 16:
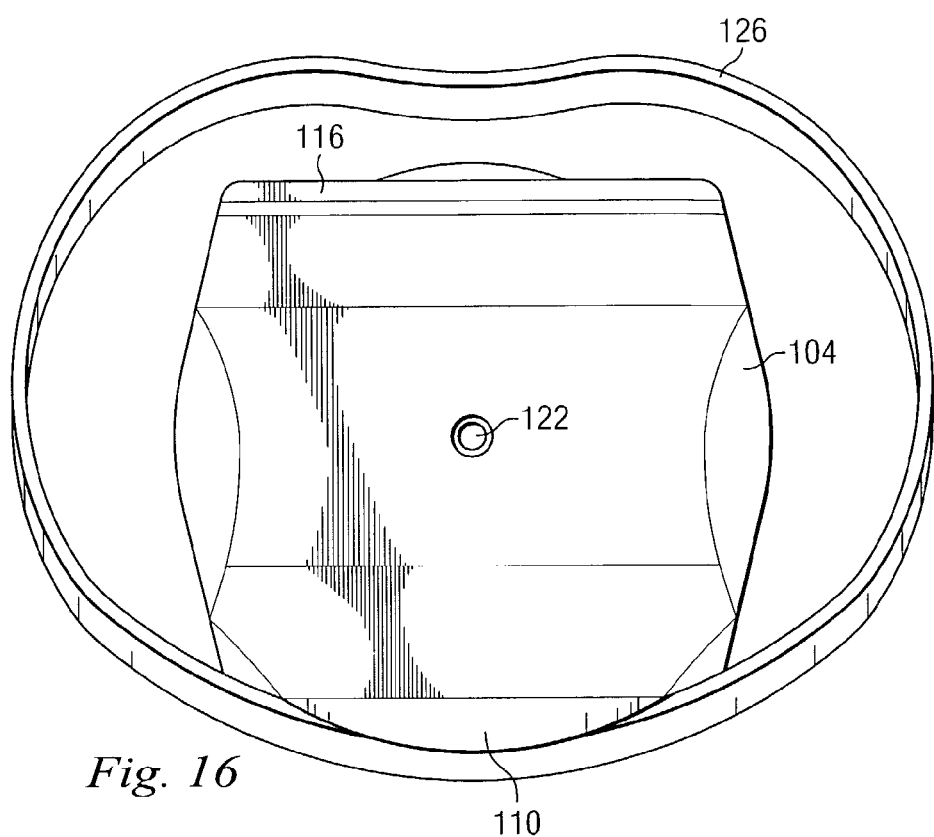
FIG. 16 is a top schematic view of one embodiment of an implanted endoprothesis.
Figure 17:
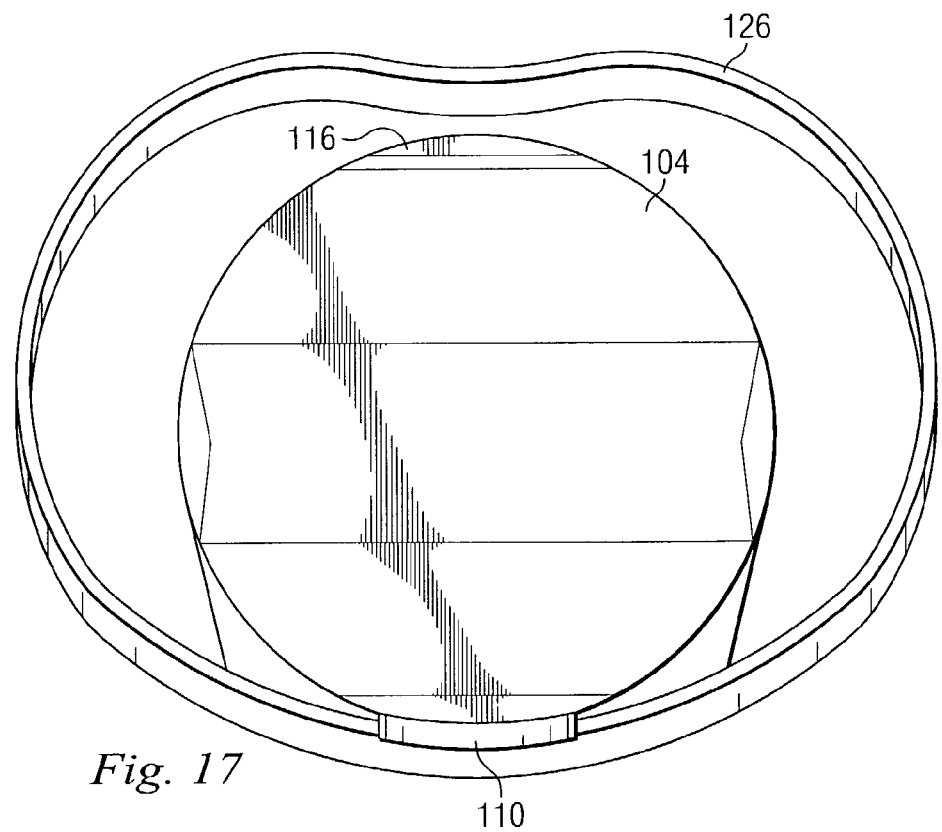
FIG. 17 is a top schematic view of one embodiment of an implanted endoprothesis.

FIG. 16 and FIG. 17 are top schematic views of two embodiments of an implanted endoprotheses. As is apparent, the lateral profile of the upper and lower members of these embodiments are slightly different; the embodiment shown in FIG. 16 has a more rectilinear profile, while the embodiment shown in FIG. 17 has a more curvilinear profile. The lateral profile of the disc space prepared to receive each of these embodiments will therefore be correspondingly different, and may require a different profile of bone removal tool.

Figure 18:
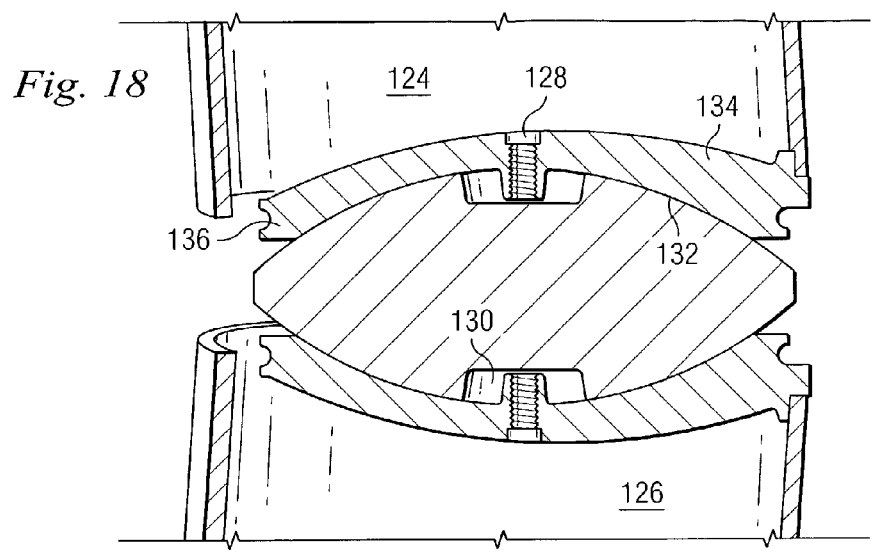
FIG. 18 is an anterior-posterior cross-sectional schematic view of an implanted endoprosthesis.

FIG. 18 provides an anterior-posterior cross-sectional schematic view of the device implanted between two vertebral bodies—the cephalad vertebral body 124 and the caudal vertebral body 126. As illustrated in FIG. 18, upper and lower members 104, 106 each include an upper centering post 128 and central member 108 includes a lower central opening 130. In accordance with this embodiment, access port 122 (shown in FIG. 12) extends through the centering post 128. Each of the upper and lower members 104, 106 also include an interior articulating surface 132 that moves over the corresponding outer surface of central member 108. In accordance with a particular embodiment, articulating surface 132 and/or the corresponding outer surface 120 of central member 108 are arcuate surfaces. The arcuate surfaces may be essentially conical, spherical or elliptical sections in nature. In addition, the interior articulating surface 132 within the upper member may be the same as, or different from, the interior articulating surface 132 within the lower member. If this is the case, the corresponding outer surface 120 of central member 108 will vary on either side thereof.

As also illustrated in FIG. 18, the caudal-cephalad thickness of upper and lower members 104, 106 may vary along the anterior-posterior axis of the device. In particular, upper and lower members 104, 106 include an enlarged anterior portion 134 and a thinner posterior portion 136. The relative thickness of posterior portion 136 of upper and lower members 104, 106 as compared to anterior portion 134 can be adjusted to vary the lordotic angle imposed on the vertebrae by the device. In accordance with a preferred embodiment, the caudal-cephalad height of the anterior portion of the device is greater than the caudal-cephalad height of the posterior portion of the device when the device is in its neutral position, i.e. the mid-point between its full flexion and extension range of motion. In accordance with an alternative embodiment, the relative height of the anterior and posterior portions of the upper shell may be the same as or different from the relative height of the anterior and posterior portions of the lower shell.

Figure 19A:
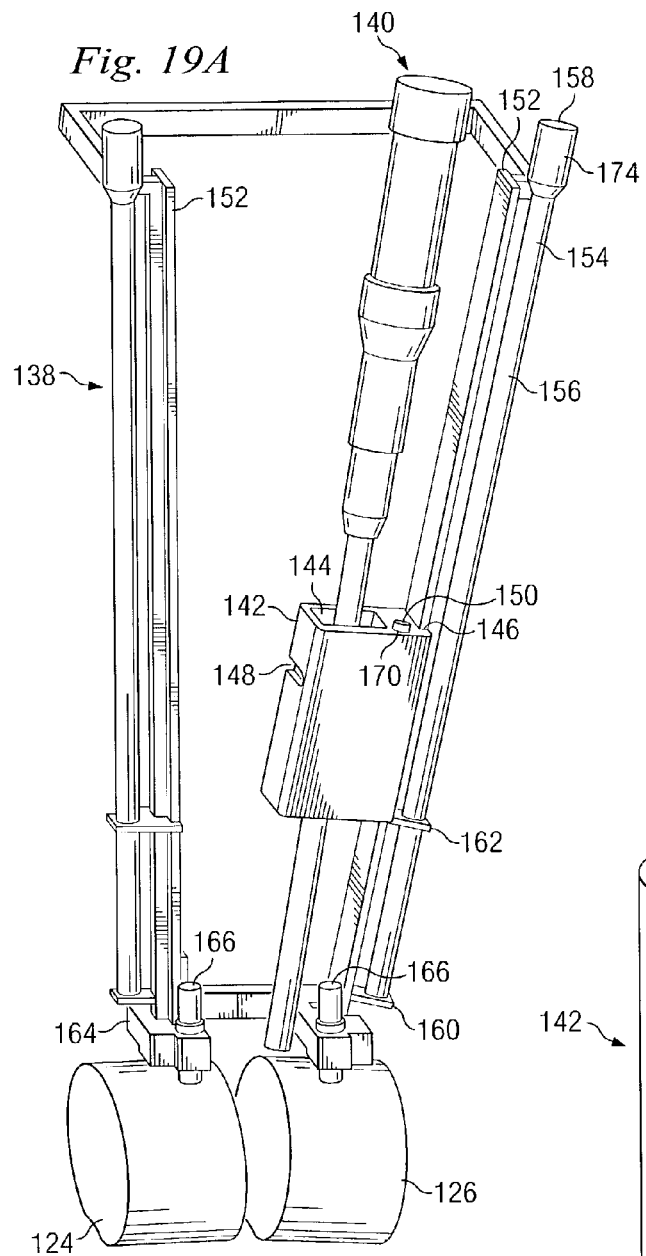
FIG. 19A is a schematic view of a bone removal device and associated support frame, and position guide block, and other instruments.

Referring now to FIG. 19, unique surgical instrumentation used to implant an endoprosthesis is provided. This instrumentation is particularly useful for preparing the vertebral disc space to receive the prostheses 102. FIG. 19A illustrates a bone removal device 140 mounted within a support frame 138 that is attached to vertebral bodies 124 and 126.

Support frame 138 consists of a base 164 and two angled guide tracks 152. In accordance with the embodiment illustrated in FIG. 19A, an upper support member 168 links the proximal ends of the two tracks 152, and enhances the rigidity of support frame 138. Base 164 is attached to the distal end of guide tracts 152, and is adapted to be attached to vertebral bodies 124, 126. In addition, base 164 may include a plurality of adjustable bushings 166 for receiving a locking mechanism, such as for example an anchor post and an anchor post nut, which locks or secures the position of the support frame 138 to the vertebral bodies.

Each angled guide track 152 extends from base 164 at an angle relative to base 164. This angle can be used to set the angle at which the bone removal tool will be introduced into the intervertebral disc space. In accordance with a preferred embodiment for use in the lumbar spine, the angle of track 152 relative to base 164 is between 0 degrees and 90 degrees. Track 152 may include a hinge that permits the user to set the angle of track 152 relative to base 164.

A position control mechanism 154 is associated with each track 152. Position control mechanism 154 includes a threaded rod 156 having a proximal end 158 and a distal end 160. Proximal end 158 includes an actuating knob 174. Distal end 160 includes a threaded segment that may or may not extend completely to the tip of distal end 160. Position control mechanism further includes a position plate 162. Position plate 162 includes a threaded opening for receiving the threaded portion of position control mechanism 154. Position plate 162 is attached to guide track 152. Desirably, position plate 162 is slideably attached to guide track 152 so that the location of position plate 162 along the length of guide track 152 may be varied.

Figure 19B:
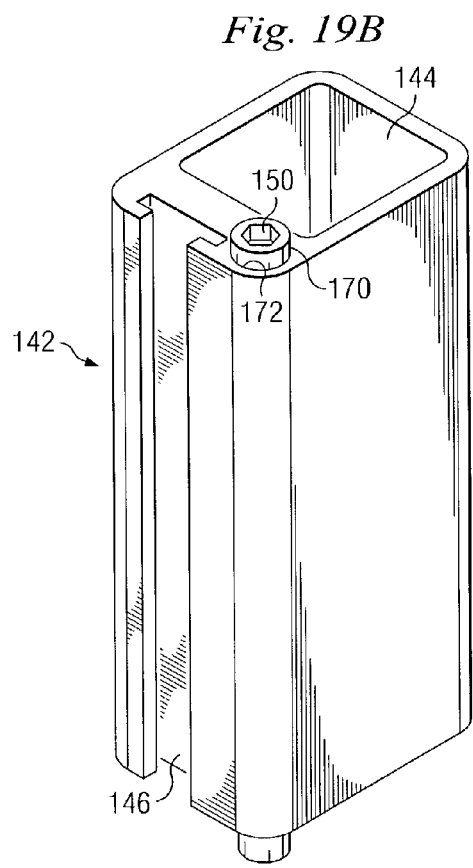
FIG. 19B is a perspective view of a position guide block shown in FIG. 19A.

A position guide block 142 is also associated with each track 152 and is shown in more detail in FIG. 19B. Position block 142 includes an axial opening 144, an axial slot 146, a pivot slot 148 (FIG. 19A), and a locking mechanism 150. Axial slot 146 is adapted to receive track 152, and enables position guide block to slide along track 152. Axial opening 144 is adapted to receive bone removal tool 140. Bone removal tool 140 includes distal and proximal pivot pins (not shown). When bone removal tool 140 is inserted into opening 144, distal and proximal pivot pins on the bone removal tool are positioned within and travel along a pivot pin slot (not shown) of position guide block 142. In accordance with a preferred embodiment, bone removal tool 140 is properly positioned within position guide block 142 when its distal pivot pin is positioned at the distal end of pivot pin slot 149 and its proximal pivot pin is aligned with pivot slot 148 of position guide block 142.

The locking mechanism 150 of position guide block 142 locks the position guide block to the position plate 162 of position control mechanism 154. In accordance with the embodiment illustrated in FIG. 19A, locking mechanism 150 includes a threaded screw 170 that passes through an axial locking mechanism opening 172 (FIG. 19B) within position guide block 142. The distal end of threaded screw is threaded into a threaded opening in position plate 162, thereby securely attaching position guide block 142 to position plate 162.

In use, support frame 138 is properly positioned over the target disc space and securely attached to the vertebral bodies, and preferably attached to an anterior surface the vertebral bodies. Support frame 138 may be properly positioned using the method and techniques described for positioning a machining jig or scaffold in U.S. patent application Ser. No. 09/923,891, filed on Aug. 7, 2001 entitled "Method and Apparatus for Stereotactic Implantation," the entire contents of which is incorporated herein by reference. Position guide block 142 is positioned along one of the tracks 152, and locking mechanism 150 is used to secure position guide block 142 to position plate 162. Bone removal device 140 is then properly positioned with position guide block 142 in the manner described hereinabove. Bone removal device 140 is then pivoted within position guide block 142 such that its proximal pivot pin (or pins) travels back and forth to the ends of pivot slot 148. While pivoting bone removal device 140, the user rotates actuating knob 174 of position control mechanism 154, thereby lowering (i.e., moving toward the vertebral bodies) position plate 162 relative to threaded rod 156. This also lowers position guide block 142, which has been locked to position plate 162 by locking mechanism 150, and thus lowers the bone removal element (not shown in FIG. 19) of bone removal device 140 into the intervertebral disc space.

Figure 20:
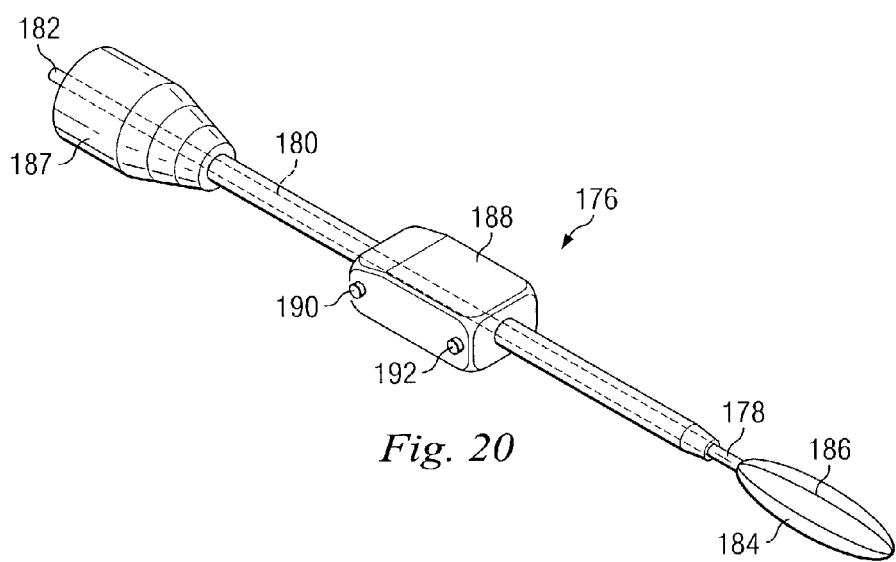
FIG. 20 is a schematic perspective view of a bone removal device suitable for use in implanting the intervertebral endoprosthesis of FIG. 12.

Bone removal device 140 may be of the type described in co-pending U.S. patent application Ser. No. 09/934,507, filed on Aug. 22, 2001, which is incorporated herein by reference. Alternatively, bone removal device 140 may be of the type illustrated in FIG. 20. In accordance with the embodiment illustrated in FIG. 20, bone removal device 140 includes a bone removal handpiece 176 and a bone removal instrument 178. Bone removal instrument 178 includes a shaft 182 and a bone removal element 184. In accordance with a preferred embodiment, bone removal element 184 consists of a cutting element and may include a plurality of cutting flutes or cutting edges 186. Bone removal handpiece 176 includes a drive connecting portion 187 positioned at its proximal end, and a hollow channel 180 extending along its length. Shaft 182 is positioned within hollow channel 180, and extends from drive connecting portion 187 of handpiece 176. In use, handpiece 176 is attached to a power source (not shown) via drive connecting portion 187. The power source may be any conventional power source such as an electric or air-powered motor. Handpiece 176 also includes positioning portion 188 that has proximal pin or stop 190 and distal pin 192.

Figure 21:
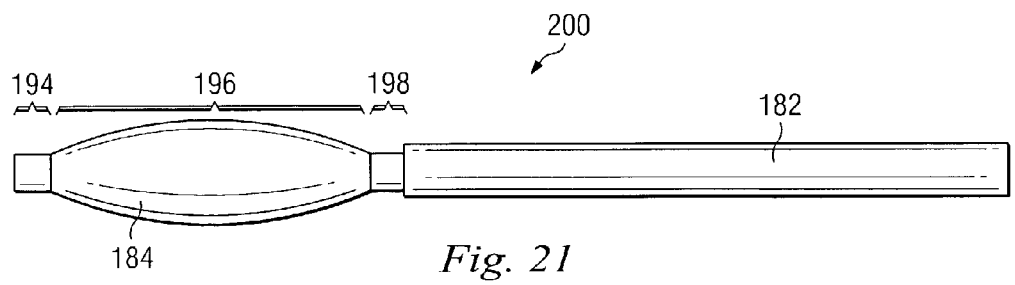
FIG. 21 is a schematic cross-sectional view of an embodiment of a bone removal instrument similar to the instrument shown in FIG. 20.

FIG. 21 illustrates the cross sectional profile of a bone removal instrument 200. In accordance with this embodiment, bone removal element 184 is connected to shaft 182, and includes a distal bone removal section 194, a central bone removal section 196, and a proximal bone removal section 198. In the embodiment illustrated, distal and proximal bone removal sections 194, 198 are substantially rectilinear, and central bone removal section 196 is substantially curvilinear or arcuate.

Figure 22:
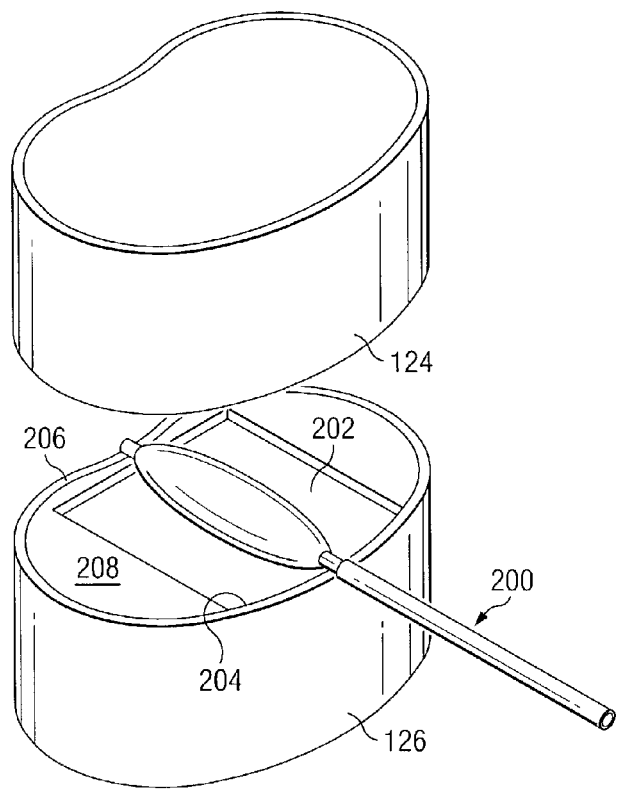
FIG. 22 is a schematic diagram illustrating the use of a bone removal instrument to remove bone from a vertebral body.

As illustrated in FIG. 22, bone removal instrument 200 may be used to create a profile 202 within an endplate of a vertebral body that matches the profile of prosthesis 102 shown in FIG. 12. In particular, bone removal instrument 200 may be inserted into handpiece 176 to form bone removal device 140 that may be inserted into axial opening 144 of position guide block 142 in the manner describe above with reference to FIG. 19. Referring again to FIG. 22, as the bone removal device is pivoted within guide block 142, proximal bone removal section 198 will form an anterior surface 204 complementary to anterior stabilizing flat 118, distal bone removal section 194 will form a posterior surface 206 complementary to posterior stabilizing flat 116, and central bone removal section 196 will form a central surface 208 that is complementary to outer surface 120 of prosthesis 102.

Those skilled in the art will appreciate that although the stabilizing flats and their complementary surfaces formed in the endplate are rectilinear in anterior-posterior direction, they will be curvilinear or arcuate in the lateral direction because of the pivoting motion of the bone removal device as it is manipulated to remove bone from the endplates. Alternatively, a lateral translation mechanism may be included as part of or to interface with one or some combination of the position guide block, the support frame, and/or the handpiece, which would enable the bone removal element to translate laterally along the endplate and create a substantially rectilinear surface in the lateral direction for a prosthesis having laterally linear stabilizing flats.

In accordance with a preferred technique, endplate profile 202 is created by multiple lateral passes of bone removal element 200 as its caudal-cephalad position is changed. In particular, a caudal-cephalad translation mechanism may be included as part of or to interface with one or some combination of the position guide block, the support frame, and/or the handpiece, which would enable the bone removal element to translate in the caudal-cephalad direction.

FIGS. 23–37 illustrate instrumentation which may be used to create endplate profile 202.

Figure 23:
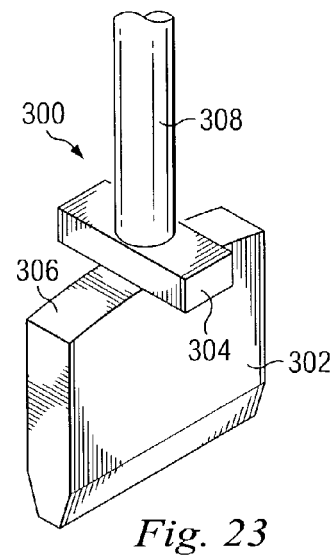
FIG. 23 is a schematic perspective view of a distal end of a sagittal wedge used in an alternative embodiment.

FIG. 23 shows a distal end of a sagittal wedge 300, which includes disc space penetrating portion 302, shoulder 304, and shaft 308. The proximal end 306 of disc penetrating portion 302 is preferably curved to approximate the profile of the anterior surface of the vertebral bodies between which it is inserted. Sagittal wedge 300 is used in the same manner as the sagittal wedge is used in the method described in U.S. application Ser. No. 09/923,891, filed on Aug. 7, 2001 entitled "Method and Apparatus for Stereotactic Implantation".

Figure 24:
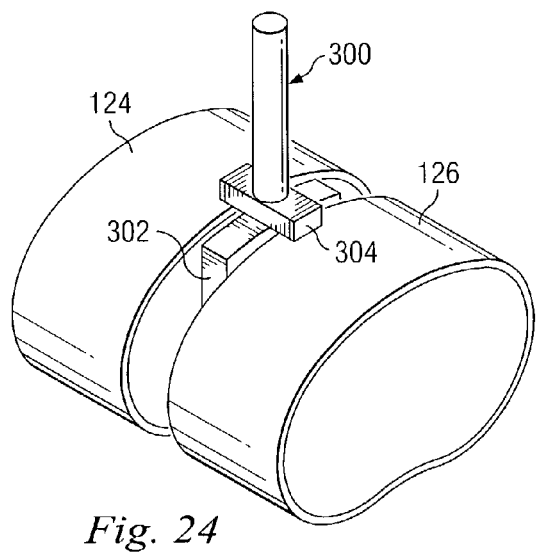
FIG. 24 is a schematic perspective view illustrating a sagittal wedge as shown in FIG. 23 inserted between two vertebral bodies.

As illustrated in FIG. 24, when sagittal wedge 300 is properly seated such that shoulder 304 rests on the anterior surfaces of the adjacent vertebral bodies, the posterior tip of disc penetrating portion 302 is positioned at approximately the anterior-posterior midpoint of the disc space. In accordance with a preferred embodiment, the anterior-posterior length of disc penetrating portion 302 is between approximately 12 mm and approximately 18 mm. In addition, the lateral dimension of disc penetrating portion 302 is up to 24 mm. As shown in FIG. 24, the lateral dimension of shoulder 304 is less than the lateral dimension of disc penetrating portion 302, which enhances the surgeon ability to view the interior of the disc space during surgery.

Figure 25:
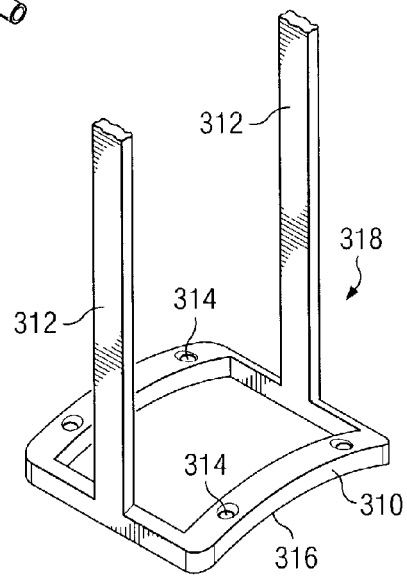
FIG. 25 is a perspective view of the distal end of a support frame used in the implantation of an intervertebral endoprosthesis in one embodiment.

FIG. 25 and FIG. 26 show a support frame 318, which includes lateral support members 312, base 310, and upper support member 342. In use, support frame 318 is positioned over sagittal wedge 300 (as illustrated in FIG. 26) in the same manner that the scaffold is placed over the sagittal wedge in U.S. application Ser. No. 09/923,891, filed on Aug. 7, 2001 entitled "Method and Apparatus for Stereotactic Implantation". Support frame 318 also serves a similar purpose as the scaffold, in that it is used to properly position instruments relative to a target intervertebral disc space.

As shown in FIG. 25, base 310 includes one or a plurality of openings 314 adapted to receive a retaining pin 332 (shown in FIG. 28) that affixes support frame 318 to the anterior surfaces of the adjacent vertebral bodies. In addition, base 310 and/or its posterior surface 316 may be curved to approximate the profile of the anterior surface of the vertebral bodies. Such a curved profile enhances the surgeon's ability to stabilize the frame's position relative to the vertebral bodies, and may improve the surgeon's field of view of the intervertebral disc space. Base 310 of support frame 318 contains a large central opening sufficient to accommodate placement of the support frame over sagittal wedge 300, and to allow introduction and manipulation of bone removal element 184 of bone removal device 140.

A disc spacer clip 320 is shown in FIG. 27, which includes upper members 322 and lower members 324. As shown in FIG. 28, clip 320 is positioned over sagittal wedge 300 after frame 318 is placed over wedge 300. Disc spacer clip 320 is positioned such that lower members 324 extend into the disc space on opposite sides of disc penetrating portion 302 of sagittal wedge 300, and upper members 322 rest on the anterior surfaces of the vertebral bodies. Upper members 322 may include at least one keyway 328 that is adapted to receive shoulder 304 of sagittal wedge 300. Upper members 322 may also include support frame interface 330, which may include an opening to enable a fixation device to securely attach disc spacer clip 320 to frame 318. As described in greater detail below, lower members 324 define a pivot saddle 326 that provides a pivot point for instruments inserted into the disc space. Disc spacer clip 320 is sized and shaped to fit within the resected annulus. Once the sagittal wedge 300 is removed, disc spacer clip 320 helps to maintain posterior distraction within the disc space.

Figure 29:
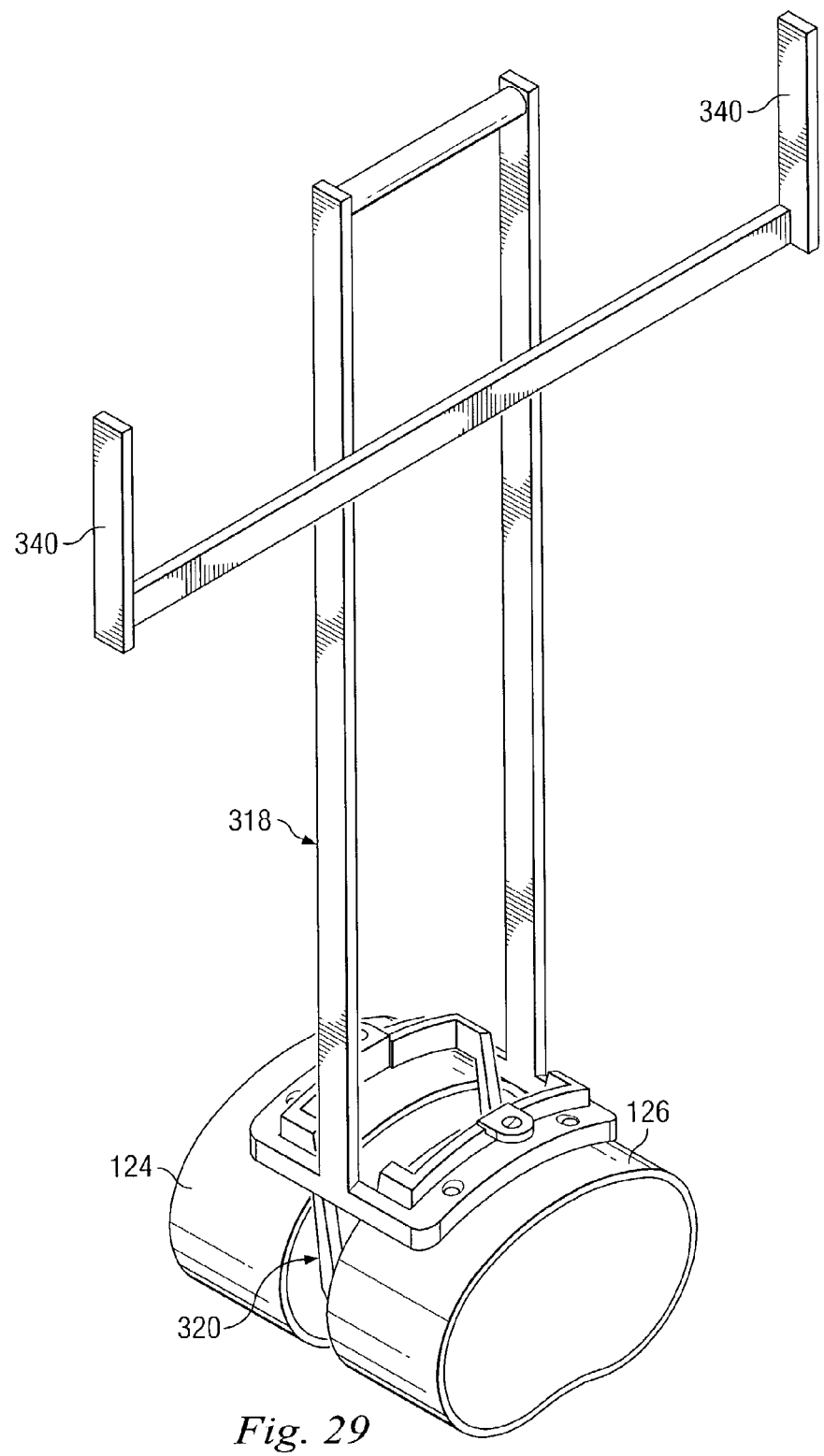
FIG. 29 is a schematic perspective view showing the arrangement of the disc spacer clip, support frame (including brace connector), and vertebral bodies after removal of the sagittal wedge.

After disc spacer clip 320 is properly positioned, support frame 318 is positioned (e.g., in the same manner as the aforementioned scaffold is positioned as described in U.S. application Ser. No. 09/923,891, filed on Aug. 7, 2001 entitled "Method and Apparatus for Stereotactic Implantation"), and its position is secured with one or more securing pins 332 shown in FIG. 28. Securing pin 332 includes a bone engager 334, shoulder 336, and shaft 338. Preferably, the bone engager 334 includes a threaded portion, and shaft 338 is flexible. Once the position of support frame 318 is secured, sagittal wedge 300 is removed, leaving only disc spacer clip 320, support frame 318 and securing pins 332, as shown in FIG. 29 (pins not shown).

Frame 318 may also include a connector for attaching the device to a brace similar to the scaffold brace described in U.S. application Ser. No. 09/923,891, filed on Aug. 7, 2001 entitled "Method and Apparatus for Stereotactic Implantation" as shown in FIG. 29, this connector may include an opening 340 adapted to receive a pin associated with the brace.

Figure 30:
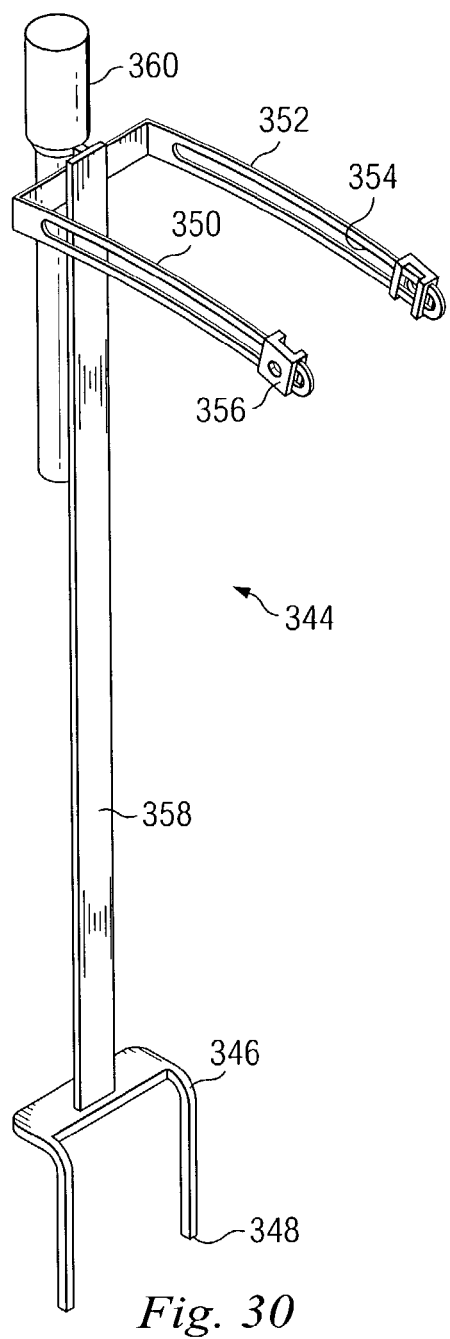
FIG. 30 is a perspective view of a tilting guide member used in implanting an intervertebral endoprosthesis.
Figure 31:
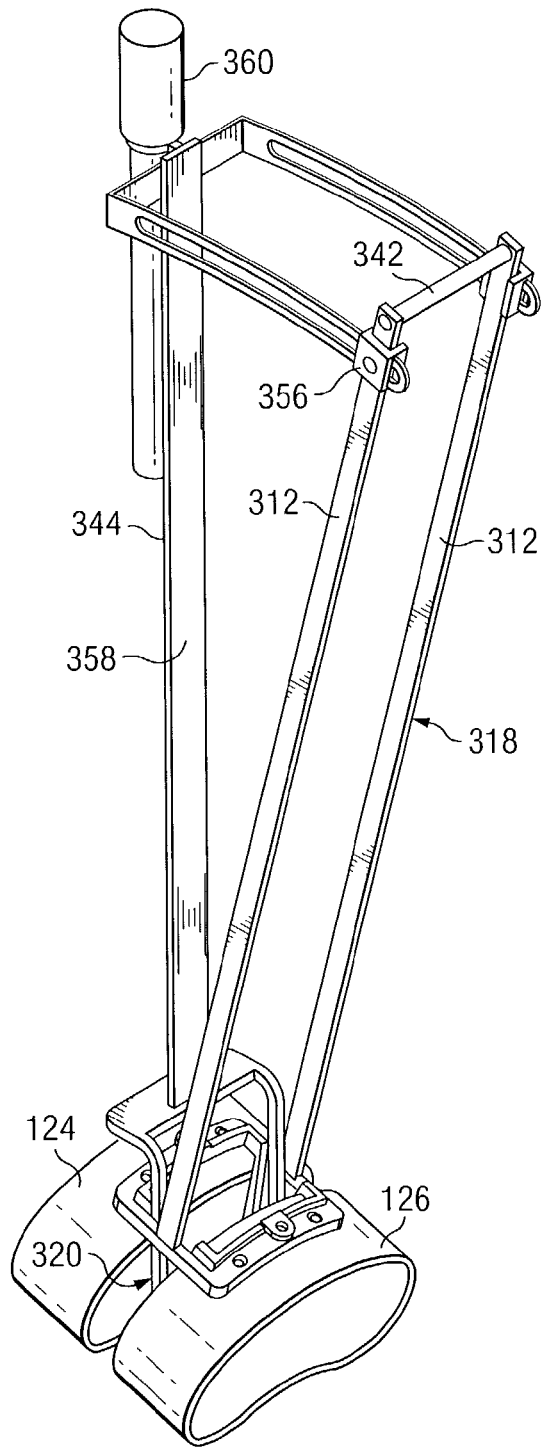
FIG. 31 is a schematic perspective view showing the arrangement of the tilting guide member of FIG. 30 with respect to the support frame, disc spacer clip, and vertebral bodies.
Figure 33:
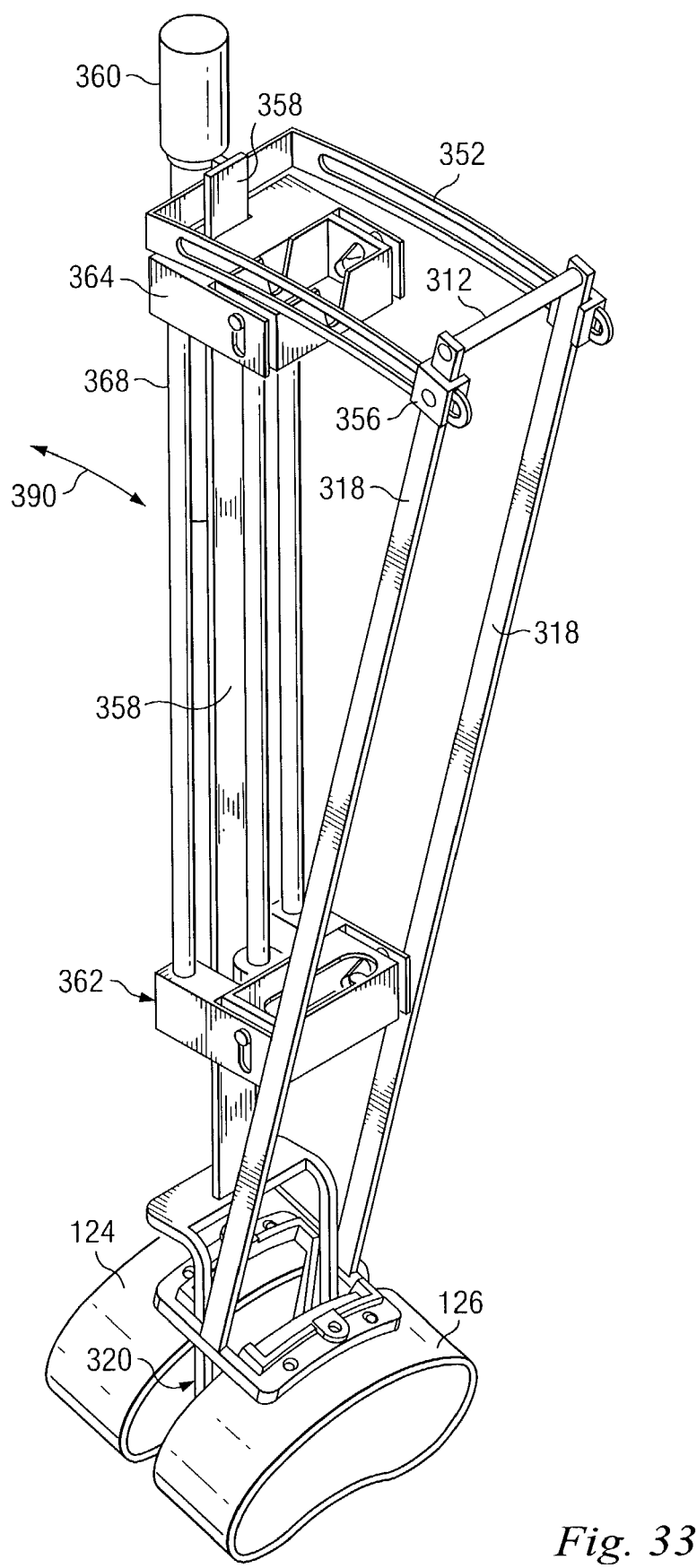
FIG. 33 is a schematic perspective view showing the arrangement of the transverse unit of FIG. 32 with respect to the assembly of FIG. 31.
Figure 34:
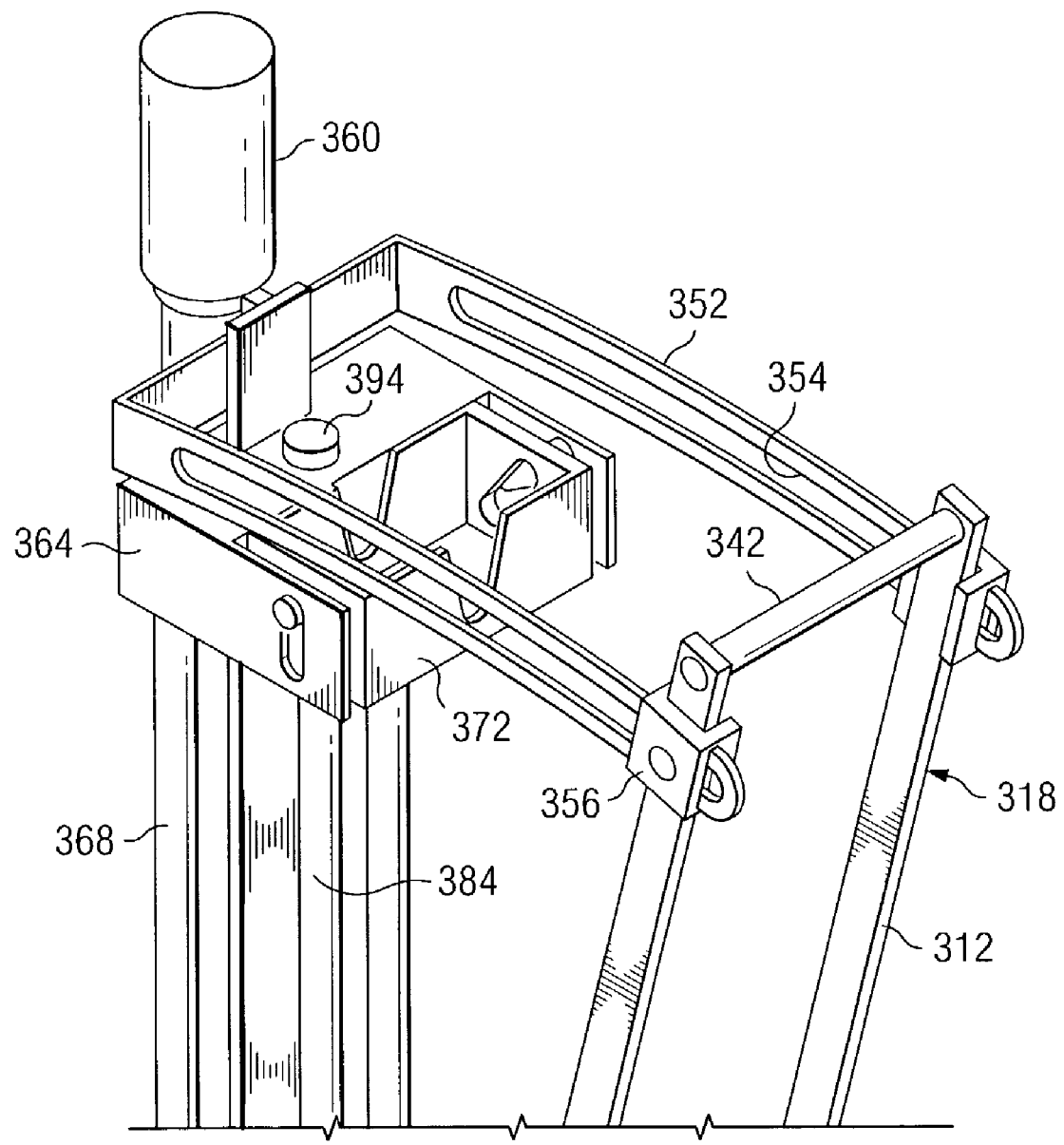
FIG. 34 is a close-up perspective view of the arrangement of FIG. 33, showing the proximal transverse block of the transverse unit.

Tilting guide member 344, which is shown in FIG. 30, is then positioned relative to the assembly of support frame 318 and disc spacer clip 320 in the manner shown in FIG. 31. Tilting guide member 344 has a distal end 346 that includes a saddle point 348, a proximal end 350 having an angle positioning and locking mechanism 352, and a mounting member 358 interconnecting distal end 346 and proximal end 350. Angle positioning and locking mechanism 352 includes an arcuate track 354 having a frame attachment member 356 slideably mounted therein. Mounting member 358 may consist of a T-track or other mechanism to facilitate slideable attachment of other instruments to tilting guide member 344. As shown in FIG. 31, tilting guide member 344 is positioned relative to the assembly of support frame 318 and disc spacer clip 320 such that the saddle point 348 is positioned in pivot saddle 326, and frame attachment member 356 is attached to the lateral support member 312 of support frame 318. Tilting guide member 344 may also include a threaded carrier 360 to control the movement along mounting member 358 of instruments positioned thereon.

This design facilitates easy and quick removal of the resulting assembly from the disc space, which is important to allow a surgeon to quickly address any surgical complications that might occur, such as vascular bleeding. The openness of the design also allows for maximum view of the surgical site. In addition, this design places the angle pivot point of mounting member 358 within the disc space. This limits the need to consider caudal-cephalad translation within the disc space in order to achieve larger angles of the instruments relative to the disc endplates. Consequently, this design is particularly useful for practicing the methods described in U.S. application Ser. No. 09/923,891, filed on Aug. 7, 2001 entitled "Method and Apparatus for Stereotactic Implantation" regarding angled milling relative to the disc space and/or the disc endplates.

Transverse unit 362 is shown in FIG. 32, and is adapted to be mounted on mounting member 358 of tilting guide member 344. The transverse unit 362 allows the bone removal device 200 to be reliably and adjustably translated toward the endplates of the vertebral bodies, and thus allows precise control over the amount of bone removed by the bone removal device 200. After the bone removal device 200 is translated to contact the endplate, it is swept laterally to remove a desired layer of tissue. The bone removal device can then be translated toward the endplate again and again swept laterally, in order to remove additional layers of material. As shown in FIG. 32A, transverse unit 362 includes a proximal transverse block 364 and a distal transverse block 366 interconnected by two lateral supports 368. Each transverse block includes an outer member 370, an inner member 372, and a central member 374 (shown more clearly in FIG. 32B). Inner member 372 includes two angled slots 376 and two opposing handpiece pivot slots 378. Outer member 370 includes two opposing slots 380, and a mounting slot 392. Mounting slot 392 is adapted to mount transverse unit 362 onto mounting member 358 (shown more clearly in FIG. 33). Central member 374 includes pins 382 that extend into angled slots 376 and outer member slots 380. As seen best in FIG. 32A, central member 374 of the proximal and distal transverse blocks are different. In particular, proximal transverse block 364 includes a handpiece opening 386 that is larger than handpiece opening 388 in distal transverse block 366.

Transverse unit 362 further includes an actuating member 384 that links the central members 374 of the proximal transverse block 364 and the distal transverse block 366. Preferably, actuating member 384 is a rod that threadably engages the central components of the proximal and distal transverse blocks, and includes actuating knob 394 (visible in FIG. 34). As actuating knob 394 is rotated, central members 374 are pulled closer together and pins 382 travel along angled slot 376 thereby causing inner member 372 to translate in the direction of arrow 390 (shown in FIG. 33), which causes any instrument mounted on transverse unit 362 to translate toward or away from the corresponding vertebral endplate.

Figure 35:
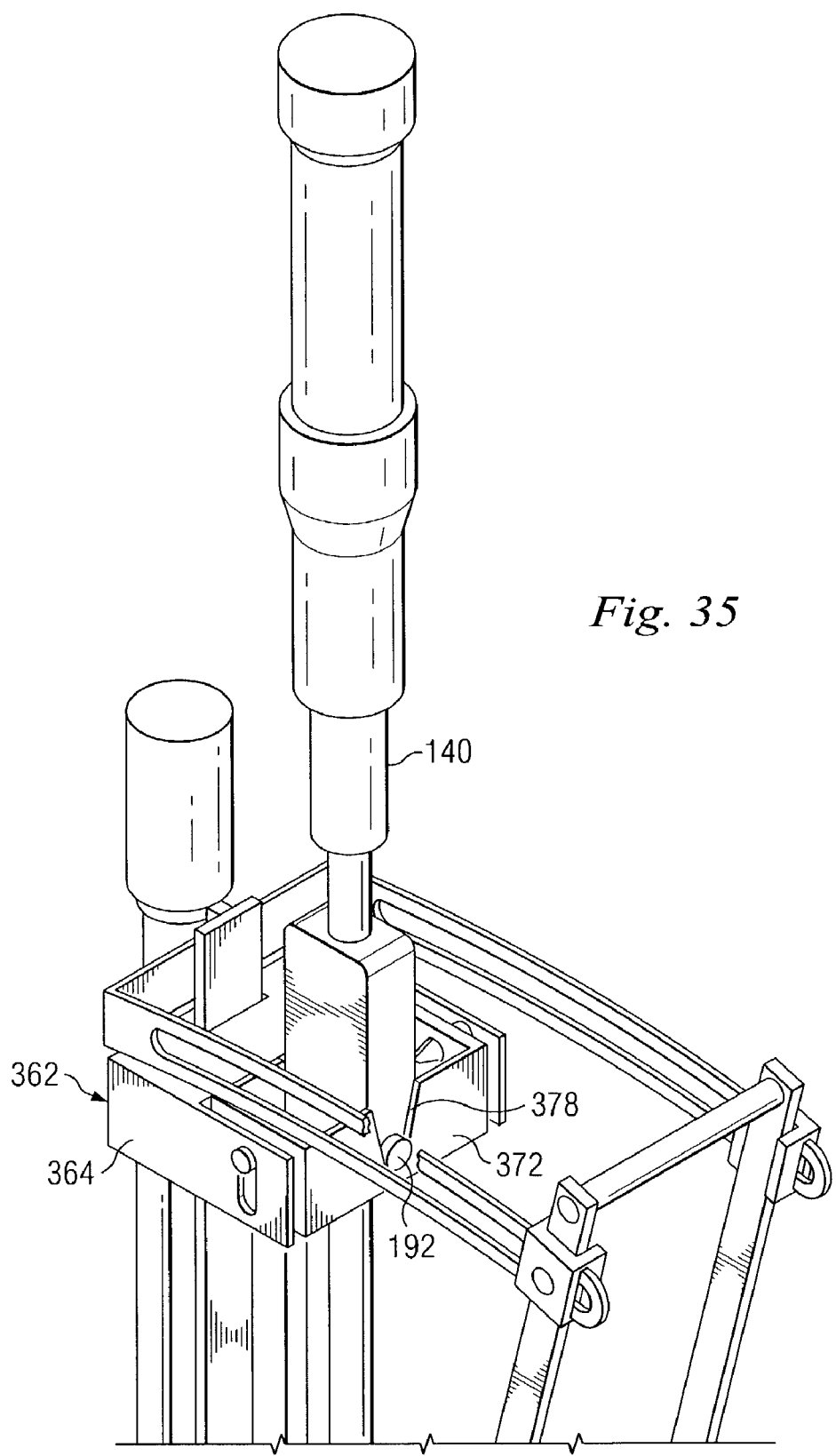
FIG. 35 is a close-up perspective view similar to that of FIG. 34, showing the disposition of a bone removal device relative to the transverse unit.
Figure 36:
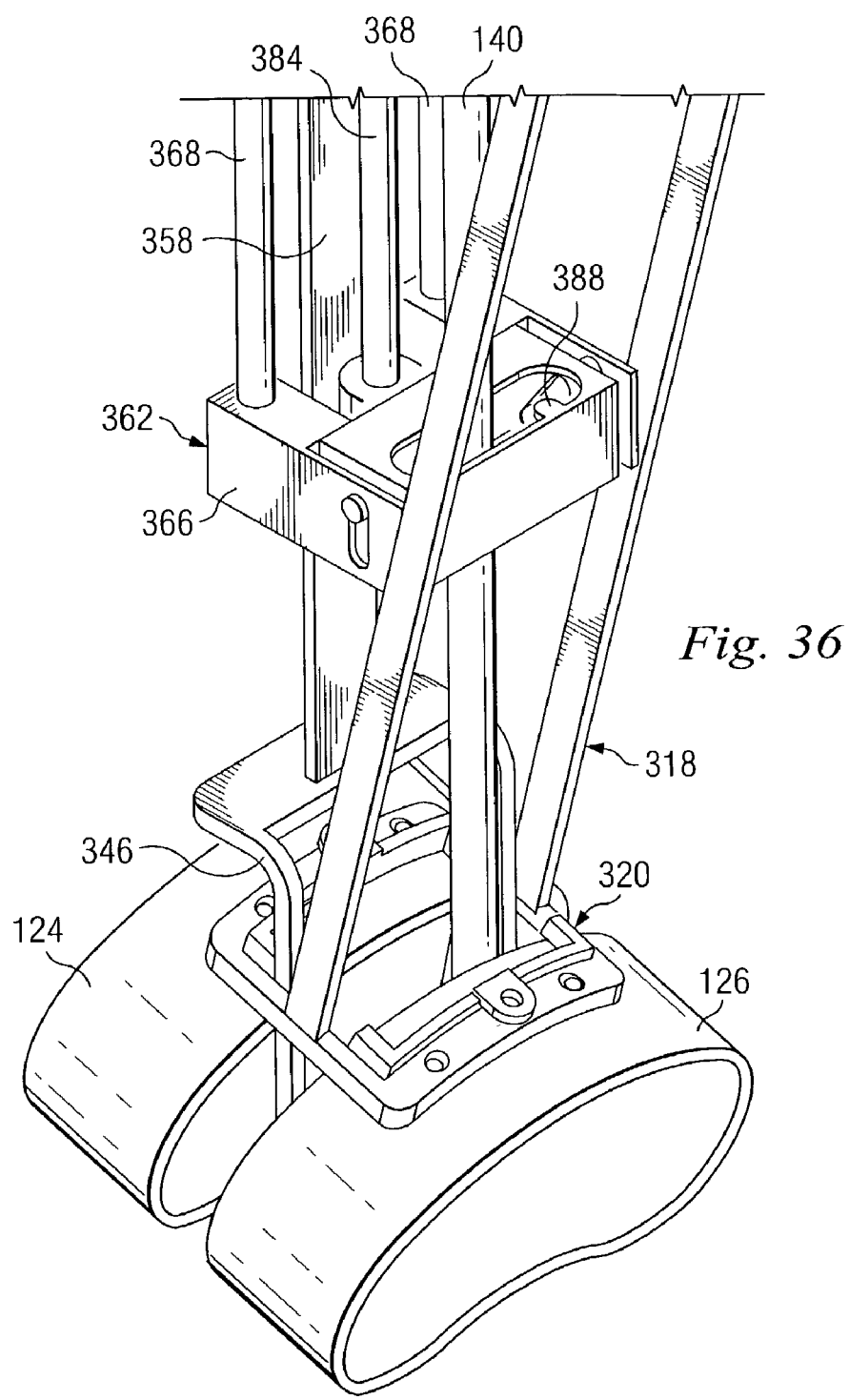
FIG. 36 is a close-up schematic perspective view showing the disposition of a bone removal device relative to the transverse unit, support frame, disc spacer clip, tilting guide member, and vertebral bodies.
Figures 37, 38A, 38B:
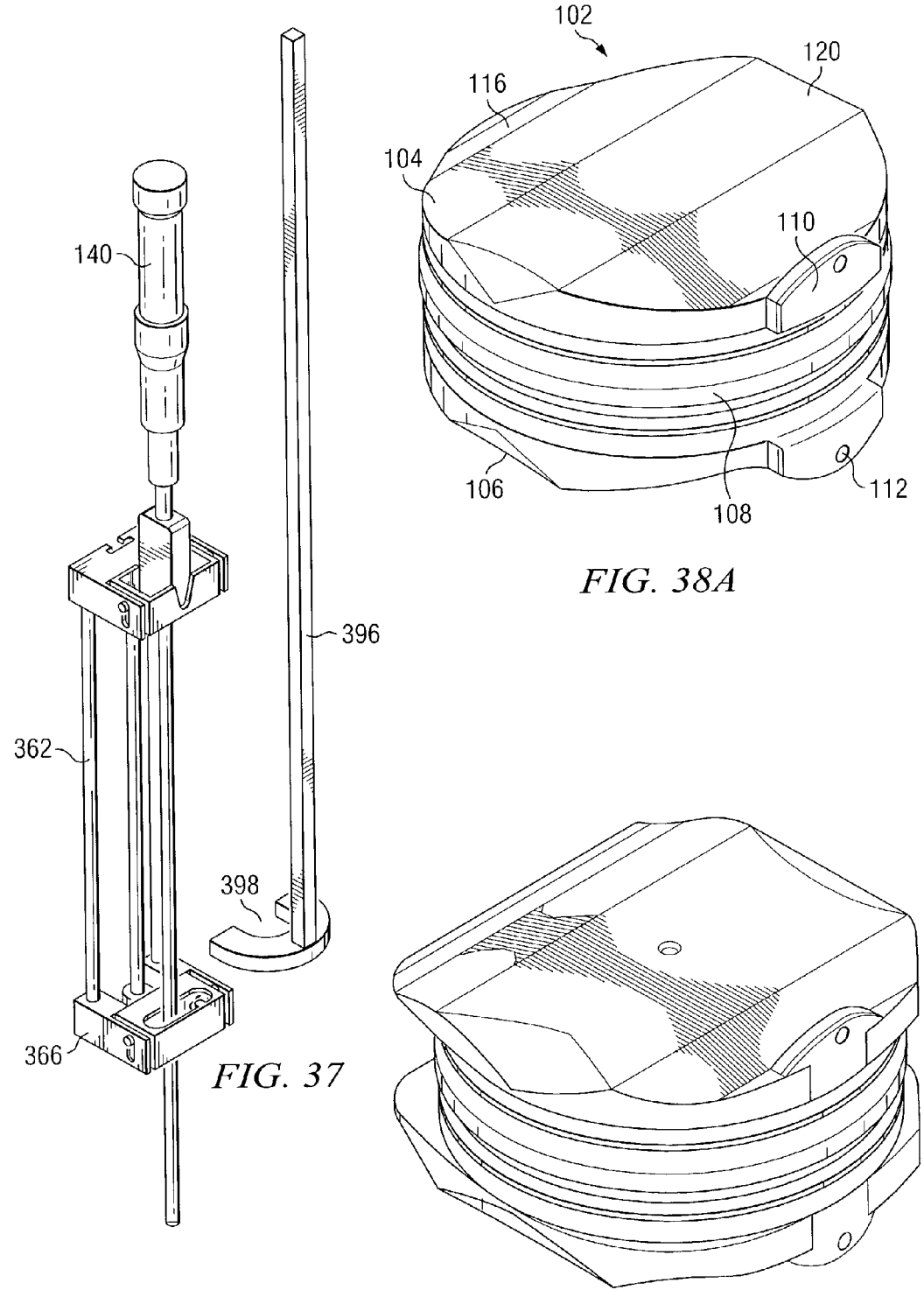

Referring now to FIGS. 35–37, bone removal device 140 is positioned within the proximal and distal handpiece openings 386, 388 of transverse unit 362 such that distal pin 192 is seated in handpiece pivot slot 378 of inner member 372 of proximal transverse block 364. Bone removal device is pivoted about pin 192 to move it laterally with respect to the vertebral endplate and translated toward or away from the vertebral endplate by turning actuating knob 394 (visible in FIG. 34) in order to guide the bone removal element (not shown) along a predetermined path to create a predetermined profile in the vertebral endplate. That predetermined profile substantially compliments the outer profile of intervertebral disc prosthesis 102. The oblong configuration of the distal handpiece opening 388 serves to guide and control the path of the cutting element, as shown in FIG. 36.

As shown in FIG. 37, a pivoting tool 396 may be used to pivot bone removal device 140. Pivot tool 396 includes a slot 398 adapted to capture the shaft of bone removal device 140. Pivot tool 396 may be inserted into the disc space such that slot 398 captures the shaft of device 140 near the distal transverse block 366. This enables the surgeon to better control the pivot motion of the bone removal device 140.

Once sufficient tissue has been removed by the bone removal device to accommodate the intervertebral endoprosthesis on one side of the disc space (using irrigation and suction to cool the bone and remove debris as described in U.S. application Ser. No. 09/923,891, filed on Aug. 7, 2001 entitled "Method and Apparatus for Stereotactic Implantation"), the procedure is repeated on the other side of the disc space by removing tissue from the opposing vertebral body. Once the disc space has been prepared, the transverse unit and/or tilting guide member may be removed, and the intervertebral endoprosthesis inserted into the prepared disc space, as described in U.S. application Ser. No. 09/923,891, filed on Aug. 7, 2001 entitled "Method and Apparatus for Stereotactic Implantation."

When the intervertebral endoprosthesis is being implanted between vertebral bodies in the lumbar region, it may be desirable to burr at least a portion of the anterior surfaces of the vertebral bodies sufficiently that wings 110 of the endoprosthesis 102 are partially or completely below the anterior surfaces of the vertebral bodies, so as to avoid contact between the wings 110 and any anatomical structures such as vessels or nerves in the lumbar region.

Two additional embodiments of intervertebral endoprostheses, suitable for implantation in the lumbar region, are shown in FIG. 38A and FIG. 38B.

The invention has been described above with respect to certain specific embodiments thereof. Those of skill in the art will understand that variations from these specific embodiments are within the spirit of the invention.

What is claimed is:

1. An implantable prosthesis, comprising:
 upper and lower rigid, opposed, biocompatible concavo-convex shells, each shell comprising:
  an outer, rough convex surface, comprising a porous coating of biocompatible material;
  an inner concave surface, comprising:
   a smooth contact area; and
   an axial post extending toward the opposing shell;
  an edge between the surfaces, comprising:
   a circumferential groove;
   a stop circumscribing the contact area of the inner concave surface and extending toward the opposing shell;
   an insertion tab extending axially away from the opposing shell; and
  a closable passage between the outer surface and the inner surface of the shell;
 a deformable, resilient central body disposed between the inner, smooth concave surfaces of the upper and lower shells, comprising:
  smooth convex upper and lower surfaces complementary and adjacent to the smooth contact area of the inner surfaces of the respective upper and lower shells;
  a shoulder circumscribing each of the smooth convex upper and lower surfaces and adapted to contact the stop of the adjacent shell and limit relative motion of the central body with respect to the shell;
  a laterally extending equatorial ridge disposed between the stop of the upper shell and the stop of the lower shell; and
  an opening in the upper and lower convex contact surfaces adapted to receive the axial post of the inner surface of each shell to limit relative motion of the central body with respect to the shell;
 an elastic sheath disposed between the upper and lower shells and surrounding the central body, comprising:
  an inner surface;
  an outer surface;
  an upper edge secured to the upper shell, and a lower edge secured to the lower shell, wherein the inner surface of the sheath and the inner surfaces of the shells define an enclosing cavity.

2. The prosthesis of claim 1 wherein the insertion tabs of the shells comprise an opening adapted to releasably engage an insertion tool.

3. The prosthesis of claim 1 further comprising an upper retaining ring formed of a biocompatible material and disposed in the circumferential groove of the upper shell for securing the upper edge of the sheath to the upper shell, and a lower retaining ring formed of a biocompatible material and disposed in the circumferential groove of the lower shell for securing the lower edge of the sheath to the lower shell.

4. An implantable prosthesis, comprising:
 upper and lower, opposed, biocompatible shells, at least one shell comprising a curved outer surface, at least one stabilizing flat extending from the outer surface, and an axial post extending towards the opposing shell;
 a central body disposed between the upper and lower shells, the central body having an opening formed therein for receiving the axial posts extending from the shells; and
 a centering post adapted for insertion into at least one of the shells, wherein the centering post comprises a threaded rod.

5. The prosthesis of claim 4 wherein the shells have a posterior portion and an anterior portion defining an axis there between and wherein the thickness of the shells varies along the anterior-posterior axis of the prosthesis.

6. The prosthesis of claim 4 wherein the shells have a rectilinear profile.

7. The prosthesis of claim 4 wherein the shells have a curvilinear profile.

8. The prosthesis of claim 4 wherein the at least one stabilizing flat comprises posterior and anterior stabilizing flats between which the curved outer surface extends.

9. The prosthesis of claim 4 wherein the at least one stabilizing flat extends away from the opposing shell.

10. The prosthesis of claim 4 wherein the upper and lower shells are adapted for implantation between a pair of lumbar vertebrae.

11. The prosthesis of claim 4 wherein at least one shell comprises a wing extending away from the opposing shell.

12. The prosthesis of claim 4 wherein an axis port extends through the centering post.

13. An implantable prosthesis, comprising:
 upper and lower, opposed, biocompatible shells, at least one shell comprising a curved outer surface, at least one stabilizing flat extending from the outer surface, and an axial post extending towards the opposing shell; and
 a central body disposed between the upper and lower shells, the central body having an opening formed therein for receiving the axial posts extending from the shells,
 wherein the shells have a posterior portion and an anterior portion wherein the anterior portion is thicker than the posterior portion.

14. The prosthesis of claim 13 wherein the shells have a posterior portion and an anterior portion defining an axis there between and wherein the thickness of the shells varies along the anterior-posterior axis of the prosthesis.

15. The prosthesis of claim 13 wherein the shells have a rectilinear profile.

16. The prosthesis of claim 13 wherein the shells have a curvilinear profile.

17. The prosthesis of claim 13 wherein the at least one stabilizing flat comprises posterior and anterior stabilizing flats between which the curved outer surface extends.

18. The prosthesis of claim 13 wherein the at least one stabilizing flat extends away from the opposing shell.

19. The prosthesis of claim 13 wherein the upper and lower shells are adapted for implantation between a pair of lumbar vertebrae.

20. The prosthesis of claim 13 wherein at least one shell comprises a wing extending away from the opposing shell.

21. The prosthesis of claim 13 further comprising a centering post adapted for insertion into at least one of the shells.

22. The prosthesis of claim 13 wherein an axis port extends through the centering post.

* * * * *